United States Patent
Brun et al.

(10) Patent No.: US 11,899,008 B2
(45) Date of Patent: Feb. 13, 2024

(54) BLOOD STATE ANALYSIS APPARATUS, BLOOD STATE ANALYSIS SYSTEM, BLOOD STATE ANALYSIS METHOD, AND PROGRAM

(71) Applicant: Sony Group Corporation, Tokyo (JP)

(72) Inventors: Marcaurele Brun, Tokyo (JP); Yoshihito Hayashi, Chiba (JP)

(73) Assignee: Sony Group Corporation, Tokyo (JP)

( * ) Notice: Subject to any disclaimer, the term of this patent is extended or adjusted under 35 U.S.C. 154(b) by 33 days.

(21) Appl. No.: 17/527,038

(22) Filed: Nov. 15, 2021

(65) Prior Publication Data

US 2022/0074921 A1     Mar. 10, 2022

Related U.S. Application Data

(62) Division of application No. 16/086,943, filed as application No. PCT/JP2016/088845 on Dec. 27, 2016, now abandoned.

(30) Foreign Application Priority Data

Mar. 30, 2016    (JP) ................. 2016-068369

(51) Int. Cl.
    *G01N 33/49*      (2006.01)
    *G01N 27/22*      (2006.01)
    (Continued)

(52) U.S. Cl.
    CPC ......... *G01N 33/4905* (2013.01); *G01N 27/02* (2013.01); *G01N 27/22* (2013.01);
    (Continued)

(58) Field of Classification Search
    CPC .. G01N 33/4905; G01N 33/86; G01N 27/026; G01N 27/221; G01N 33/49;
    (Continued)

(56) References Cited

U.S. PATENT DOCUMENTS

| | | |
|---|---|---|
| 6,432,657 B1 | 8/2002 | Kikuchi et al. |
| 2012/0035450 A1 | 2/2012 | Hayashi |

(Continued)

FOREIGN PATENT DOCUMENTS

| | | |
|---|---|---|
| JP | 2010-513095 A1 | 4/2010 |
| JP | 2010-518371 A | 5/2010 |

(Continued)

OTHER PUBLICATIONS

International Search Report and English translation thereof dated Mar. 28, 2017 in connection with International Application No. PCT/JP2016/088845.

(Continued)

*Primary Examiner* — Dean Kwak
(74) *Attorney, Agent, or Firm* — Wolf, Greenfield & Sacks, P.C.

(57) ABSTRACT

A blood state analysis apparatus including at least an analysis unit that uses data related to the temporal change in electrical characteristics to analyze information related to fibrinogen in a blood sample, in which the analysis unit uses at least two predetermined time points derived from the data related to the temporal change on a basis of a predetermined mathematical definition to calculate a parameter R, and acquires at least two pieces of information related to the fibrinogen in the blood sample.

5 Claims, 10 Drawing Sheets

(51) Int. Cl.
  *G01N 33/68* (2006.01)
  *G01N 33/86* (2006.01)
  *G01N 27/02* (2006.01)

(52) U.S. Cl.
  CPC ......... *G01N 33/6896* (2013.01); *G01N 33/86* (2013.01); *G01N 2333/75* (2013.01); *G01N 2440/14* (2013.01); *G01N 2800/2821* (2013.01)

(58) Field of Classification Search
  CPC .............. G01N 27/02; G01N 27/021; G01N 33/48707; G01N 15/05; G01N 27/028; G01N 27/22; G01N 2015/055; G01N 2333/75; G01N 2333/805; G01N 2011/0066; G01N 2440/14; G01N 35/00722; G01N 33/6896; G01N 2800/2821
  See application file for complete search history.

(56) References Cited

U.S. PATENT DOCUMENTS

| | | | |
|---|---|---|---|
| 2012/0238026 A1 | 9/2012 | Hayashi et al. | |
| 2015/0077144 A1 | 3/2015 | Hayashi et al. | |
| 2017/0030891 A1 | 2/2017 | Brun et al. | |
| 2017/0212097 A1* | 7/2017 | Katsumoto | G01N 33/48707 |
| 2019/0101526 A1 | 4/2019 | Brun et al. | |

FOREIGN PATENT DOCUMENTS

| | | |
|---|---|---|
| JP | 2012-194067 A | 10/2012 |
| JP | 2012-194087 A | 10/2012 |
| JP | 2013-221782 A | 10/2013 |
| JP | 2015-028500 A | 2/2015 |
| JP | WO 2015/159623 A1 | 4/2017 |
| WO | WO 99/05312 A1 | 2/1999 |
| WO | WO 2013/153735 A1 | 10/2013 |
| WO | WO 2015/159623 A1 | 10/2015 |
| WO | WO-2016013176 A1 * | 1/2016 ........... G01N 27/221 |

OTHER PUBLICATIONS

Written Opinion and English translation thereof dated Mar. 28, 2017 in connection with International Application No. PCT/JP2016/088845.

International Preliminary Report on Patentability and English translation thereof dated Oct. 11, 2018 in connection with International Application No. PCT/JP2016/088845.

Japanese Office Action dated Aug. 18, 2020 in connection with Japanese Application No. 2018-508397 and English translation thereof.

Alkjaersig et al., Pathogenesis of the Coagulation Defect Developing During Pathological Plasma Proteolytic ('Fibrinolytic') States. II The Significance, Mechanism and Consequences of Defective Fibrin Polymerization, Journal of Clinical Investigation, 1962, vol. 41, No. 4, submitted for publication Jul. 13, 1961; accepted Dec. 21, 1961, pp. 917-934.

Cunningham et al., Laboratory Diagnosis of Dysfibrinogenemia, Arch Pathol Lab Med, Apr. 2002, vol. 126, pp. 499-505.

Green et al., Association of Abnormal Fibrin Polymerisation with Severe Liver Disease, Gut, 1977, vol. 18, pp. 909-912.

Llobet et al., An Acquired Inhibitor that Produced a Delay of Fibrinopeptide B Release in an Asymptomatic Patient, Haematologica 2007, 92:(2):e17-e19, http://www.haematologica.org/content/92/2/e17, last accessed Sep. 6, 2018.

Nakayama-Hamada et al., Citrullinated Fibrinogen Inhibits Thrombin-catalysed Fibrin Polymerization, J. Biochem, 2008, vol. 144; pp. 393-398.

Rosenberg et al., A New Haemorrhagic Disorder with Defective Fibrin Stabilization and Cryofibrinogenaemia, British Journal of Haematology, http://onlinelibrary.wiley.com/doi/10.1111/j.1365-2141.1974.tb00472.x/abstact, retrieved Jun. 15, 2016, 1974, vol. 26, pp. 269-284, last accessed Sep. 6, 2018.

* cited by examiner

BLOOD STATE ANALYSIS APPARATUS, BLOOD STATE ANALYSIS SYSTEM, BLOOD STATE ANALYSIS METHOD, AND PROGRAM

CROSS-REFERENCE TO RELATED APPLICATIONS

The present application claims the benefit under 35 U.S.C. § 120 as a divisional application of U.S. application Ser. No. 16/086,943, filed on Sep. 20, 2018, which claims the benefit under 35 U.S.C. § 371 as a U.S. National Stage Entry of International Application No. PCT/JP2016/088845, filed in the Japanese Patent Office as a Receiving Office on Dec. 27, 2016, which claims priority to Japanese Patent Application Number JP2016-068369, filed in the Japanese Patent Office on Mar. 30, 2016, each of which is hereby incorporated by reference in its entirety.

TECHNICAL FIELD

The present technology relates to a blood state analysis apparatus. More specifically, the present technology relates to a blood state analysis apparatus, a blood state analysis system, a blood state analysis method, and a program that are capable of acquiring, in a single measurement, a plurality of pieces of information related to fibrinogen, when measuring the electrical characteristics of a blood sample.

BACKGROUND ART

In the past, it has been known that there is a pathological condition in which a disorder of the blood clotting process at any stage causes abnormal blood clotting. Examples of the pathological condition include hemophilia caused by deficiency or reduction in activity of factor VIII or factor IX among blood clotting factors, thrombocytopenia, and hypofibrinogenemia.

For such a pathological condition, it is usual to examine the blood clotting function by using an analysis apparatus employing thromboelastography (TEG), thromboelastometry (ROTEM), dielectric blood coagulometry (DBCM), or the like (see, for example, Patent Literature 1 and 2). By combining these analysis apparatuses, it is possible to distinguish between thrombocytopenia and hypofibrinogenemia.

Further, the present inventors have proposed "a blood state analysis apparatus including at least an analysis unit that evaluates, on the basis of data related to the temporal change in electrical characteristics measured at a specific frequency or within a specific frequency band from two or more blood samples prepared from one blood specimen and having different agent types or concentrations, the effect of the agent or a factor in the blood on the coagulation system or fibrinolytic system of the blood" in Patent Literature 3.

Here, the following pathological condition is known as a pathological condition in which fibrinogen is not normally changed into fibrin while the amount itself of fibrinogen is normal.

For example, Non-Patent Literature 1 discloses "dysfibrinogenaemia". In this pathological condition, symptoms such as abnormality of response to thrombin and the like, decrease in blood clotting ability, and decrease in function of the fibrinolytic system appear genetically or acquiredly (e.g., due to decrease in liver function, hepatitis, or liver cancer) due to the structural problem of fibrinogen. Meanwhile, the amount itself of fibrinogen is normal. Further, Non-Patent Literature 2 discloses "blood clotting disorder due to fibrinogen proteolysis". This pathological condition is a blood clotting disorder that appears after surgical trauma or birth complications and is caused by the function (residual substance) of the fibrinolytic system. Further, Cited References 3 to 5 disclose, as a kind of autoimmune disease, a fibrinogen polymerization disorder due to an IgG antibody and a disorder due to citrullinated fibrinogen.

In the past, it has been know that diagnosis of the pathological condition in which fibrinogen is not normally changed into fibrin while the amount itself of fibrinogen is normal as described above is very complicated, and requires at least two types of examination (see, for example, Patent Literature 6). Specifically, the examination is generally performed on the basis of comparison of the amount of fibrinogen by prolonging thrombin time and measuring an antibody.

CITATION LIST

Patent Literature

Patent Literature 1: Japanese Unexamined Patent Application Publication No. 2010-513905
Patent Literature 2: Japanese Unexamined Patent Application Publication No. 2010-518371
Patent Literature 3: WO 2015/159623

Non-Patent Literature

Non-Patent Literature 1: "Association of abnormal fibrin polymerization with severe liver disease", G. Green et al., Gut, 1977, 18, 909-912
Non-Patent Literature 2: "PATHOGENESIS OF THE COAGULATION DEFECT DEVELOPING DURING PATHOLOGICAL PLASMA PROTEOLYTIC ("FIBRINOLYTIC") STATES.", N. Alkjaersig et al., Journal of Clinical Investigation, 1962, Vol. 41, No. 4
Non-Patent Literature 3: "A New Haemorrhagic Disorder with Defective Fibrin Stabilization and Cryofibrinogenaemia" R. D. Rosenberg et al., British Journal of Haematology, Volume 26, Issue 2, 269-284, February 1974
Non-Patent Literature 4: "An acquired inhibitor that produced a delay of fibrinopeptide B release in an asymptomatic patient" D. Llobet et al., Haematologica February 2007 92: e17-e19
Non-Patent Literature 5: "Citrullinated fibrinogen inhibits thrombin-catalysed fibrin polymerization." Nakayama-Hamada M et al., J Biochem. 2008 September; 144(3): 393-8, 2008 Jun. 26
Non-Patent Literature 6: "Laboratory Diagnosis of Dysfibrinogenemia" Mark T. Cunningham et. al., Archives of Pathology & Laboratory Medicine: April 2002, Vol. 126, No. 4, pp. 499-505

DISCLOSURE OF INVENTION

Technical Problem

However, in the existing analysis apparatus, since the end point of blood clotting is used for analysis, it has been difficult to perform evaluation reflecting the process of blood clotting. In particular, it has been difficult to perform evaluation when there is a disorder in the process of generating fibrin by fibrinogen polymerization. In particular, there has been a problem that two types of examination are required for diagnosis of, for example, a pathological condition in which fibrinogen is not normally changed into fibrin while the amount itself of fibrinogen is normal.

In view of the above, it is a main object of the present technology to provide a technology capable of acquiring, in a single measurement, a plurality of pieces of information related to fibrinogen, when measuring the electrical characteristics of a blood sample.

Solution to Problem

That is, in the present technology, first, a blood state analysis apparatus, including: at least
an analysis unit that uses data related to a temporal change in electrical characteristics to analyze information related to fibrinogen in a blood sample, in which
the analysis unit uses at least two predetermined time points derived from the data related to the temporal change on a basis of a predetermined mathematical definition to calculate a parameter R, and acquires at least two pieces of information related to the fibrinogen in the blood sample
is provided.

In the blood information analysis apparatus according to the present technology, the at least two predetermined time points may be selected from
(i) a time point when the electrical characteristics have a maximum value or a minimum value, or a time point when a change in the electrical characteristics exceeds a predetermined threshold value,
(ii) a time point when the change in the electrical characteristics exceeds a predetermined change rate set in advance, or a time point when the change in the electrical characteristics falls below the predetermined change rate set in advance,
(iii) a time point when the change in the electrical characteristics is the maximum or a middle time point between the (i) and the (ii), and
(iv) a time point when a maximum change rate is obtained between the (i) and the (ii). In this case, the analysis unit may compare the at least two predetermined time points selected from the (i) to (iv) with each other on a basis of a predetermined starting point.

In the blood information analysis apparatus according to the present technology, the information may include at least two pieces of information selected from information related to a total amount of fibrinogen, information related to an amount of fibrinogen involved in blood clotting, and information related to a polymerization ability of fibrinogen.

In the blood information analysis apparatus according to the present technology, the electrical characteristics may include a dielectric constant at a specific frequency.

In the blood information analysis apparatus according to the present technology, the analysis unit may further use a derivative to calculate a parameter S, the derivative being obtained at a time point before the electrical characteristics has a maximum value or a minimum value.

In the blood information analysis apparatus according to the present technology, the analysis unit may further use a blood clotting amplitude to calculate a parameter A, the blood clotting amplitude being obtained at a predetermined time point.

Further, in the present technology, also a blood state analysis system, including: at least
a measurement unit that measures electrical characteristics of a blood sample over time; and
an analysis unit that uses data related to a temporal change in the electrical characteristics measured by the electrical characteristics measurement apparatus to analyze information related to fibrinogen in the blood sample, in which
the analysis unit uses at least two predetermined time points derived from the data related to the temporal change on a basis of a predetermined mathematical definition to calculate a parameter R, and acquires at least two pieces of information related to the fibrinogen in the blood sample
is provided.

The blood information analysis system according to the present technology may further include
a server that stores the data related to the temporal change by the electrical characteristics measurement apparatus and/or an analysis result by the blood state analysis apparatus, in which
the server is connected to the electrical characteristics measurement apparatus and/or the blood state analysis apparatus via a network.

Further, in the present technology, also a blood state analysis method, including: at least
a measurement step of measuring electrical characteristics of a blood sample over time; and
an analysis step of using data related to a temporal change in the electrical characteristics acquired in the measurement step to analyze information related to fibrinogen in the blood sample, in which
the analysis step further includes using at least two predetermined time points derived from the data related to the temporal change on a basis of a predetermined mathematical definition to calculate a parameter R, and acquiring at least two pieces of information related to the fibrinogen in the blood sample
is provided.

In the blood information analysis method according to the present technology, the parameter may be selected from
(i) a time point when the electrical characteristics have a maximum value or a minimum value, or a time point when a change in the electrical characteristics exceeds a predetermined threshold value,
(ii) a time point when the change in the electrical characteristics exceeds a predetermined change rate set in advance, or a time point when the change in the electrical characteristics falls below the predetermined change rate set in advance,
(iii) a time point when the change in the electrical characteristics is the maximum or a middle time point between the (i) and the (ii), and
(iv) a time point when a maximum change rate is obtained between the (i) and the (ii). In this case, the analysis step may further include comparing the at least two predetermined time points selected from the (i) to (iv) with each other on a basis of a predetermined starting point.

In the blood information analysis method according to the present technology, the information may include at least two pieces of information selected from information related to a total amount of fibrinogen, information related to an amount of fibrinogen involved in blood clotting, and information related to a polymerization ability of fibrinogen.

In the blood information analysis method according to the present technology, the analysis step may further include using a derivative to calculate a parameter S, the derivative being obtained at a time point before the electrical characteristics has a maximum value or a minimum value.

In the blood information analysis method according to the present technology, the analysis step may further include using a blood clotting amplitude to calculate a parameter A, the blood clotting amplitude being obtained at a predetermined time point.

In addition, in the present technology, also a program that causes a computer to function as:
a measurement unit that measures electrical characteristics of a blood sample over time; and
an analysis unit that uses data related to a temporal change in the electrical characteristics acquired by the measurement unit to analyze information related to fibrinogen in the blood sample, in which
the analysis unit uses at least two predetermined time points derived from the data related to the temporal change on a basis of a predetermined mathematical definition to calculate a parameter R, and acquires at least two pieces of information related to the fibrinogen in the blood sample
is provided.

Advantageous Effects of Invention

According to the present technology, it is possible to acquire, in a single measurement, a plurality of pieces of information related to fibrinogen, when measuring the electrical characteristics of a blood sample. It should be noted that the effect described here is not necessarily limitative and may be any effect described in the present disclosure.

Figure 2:
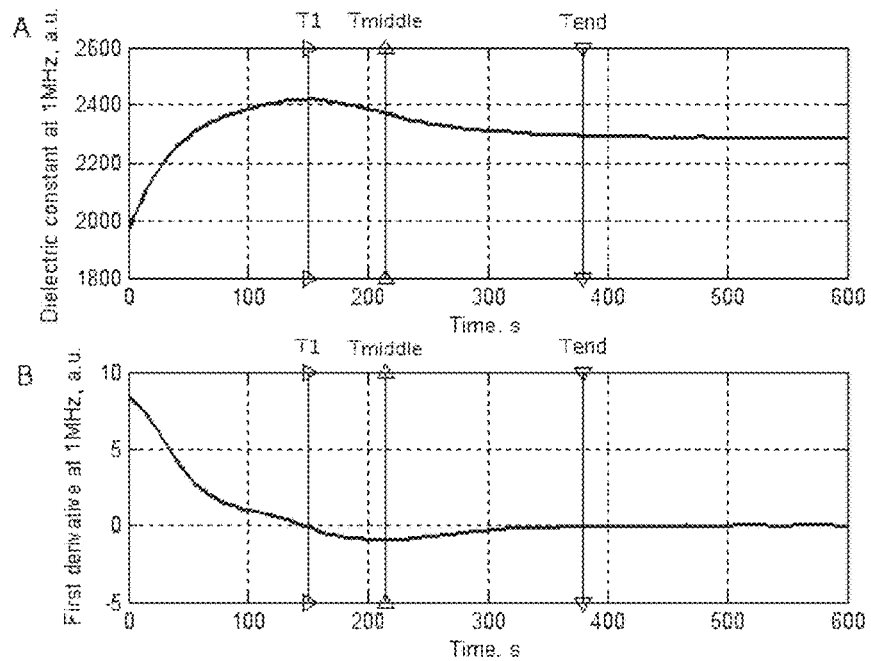

Part A of FIG. 2 is a drawing substitute graph showing data related to the temporal change of the first 10 minutes of the blood clotting reaction at the dielectric constant of 1 MHz in the case of measuring blood of a healthy subject, and Part B of FIG. 2 is a drawing substitute graph showing the first-order derivative of the data related to the temporal change shown in Part A.

Figure 3:
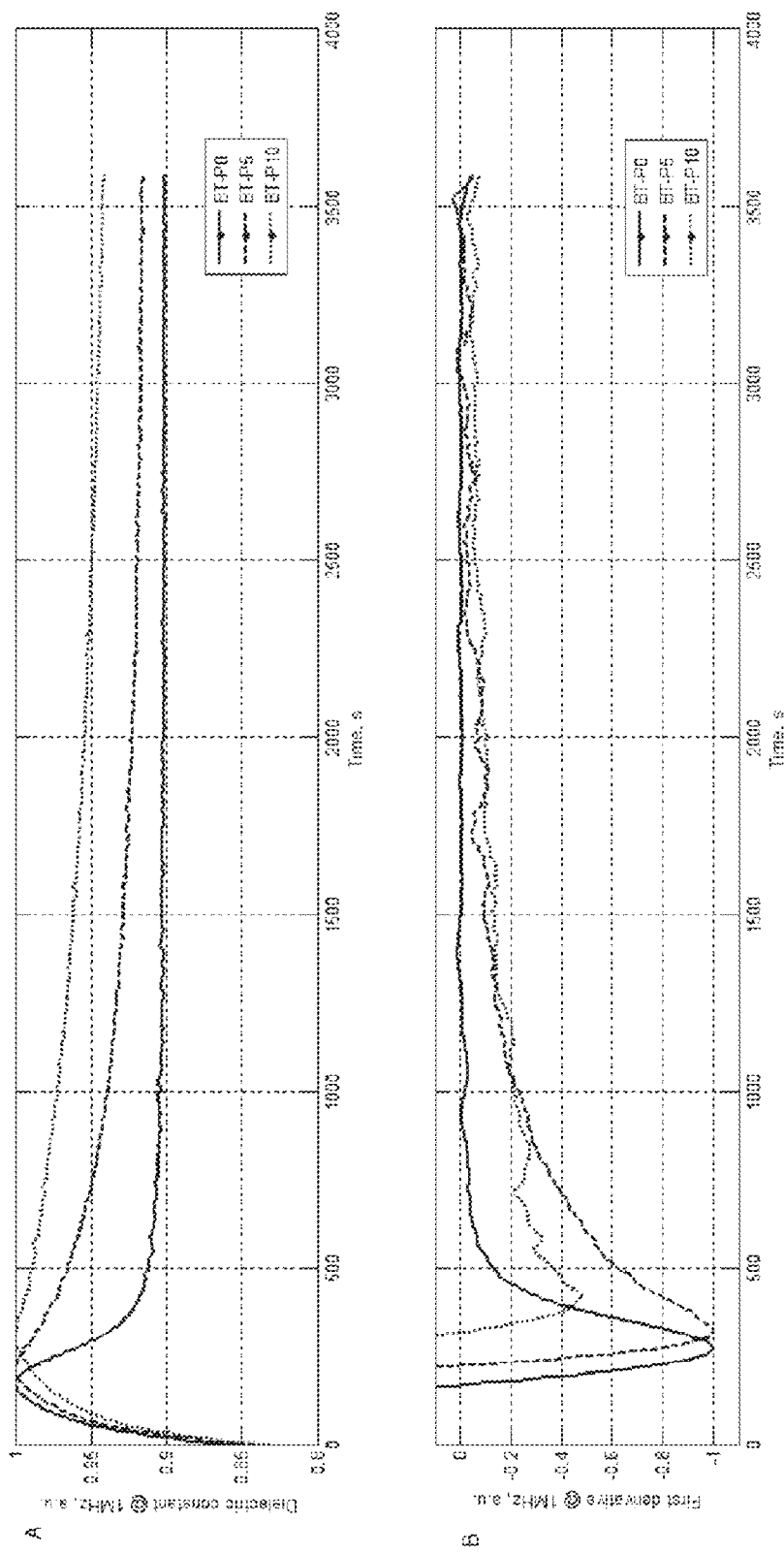

Part A of FIG. 3 is a drawing substitute graph showing the data related to the temporal change of the blood clotting reaction at the dielectric constant of 1 MHz in the case of measuring those to which blood clotting fibrinogen polymerization inhibitors having three concentrations are added, and Part B of FIG. 3 is a drawing substitute graph showing the first-order derivative of the data related to the temporal change shown in Part A.

Figure 4:
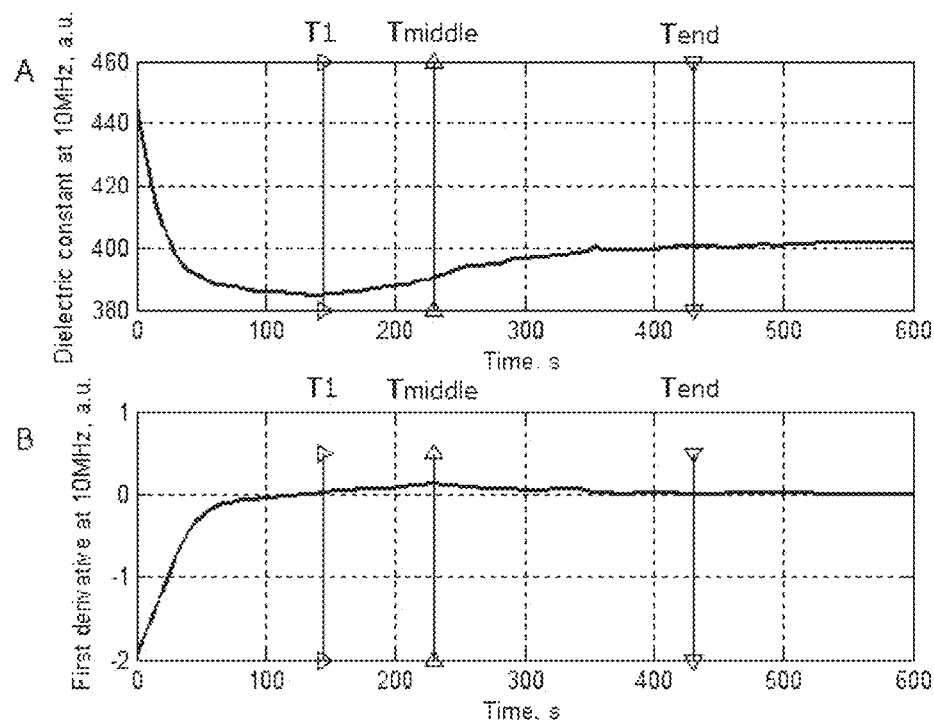

Part A of FIG. 4 is a drawing substitute graph showing data related to the temporal change of the first 10 minutes of the blood clotting reaction at the dielectric constant of 10 MHz in the case of measuring blood of a healthy subject, and Part B of FIG. 4 is a drawing substitute graph showing the first-order derivative of the data related to the temporal change shown in Part A.

Figure 5:
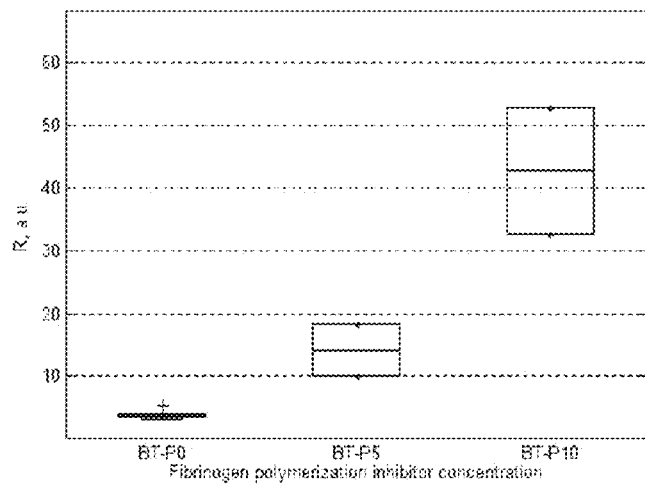

FIG. 5 a drawing substitute graph showing the relationship between the parameter R and added fibrinogen polymerization inhibitors (BT-P0, BT-P5, and BT-P10) in the case of performing measurement at the dielectric constant of 1 MHz.

Figure 6:
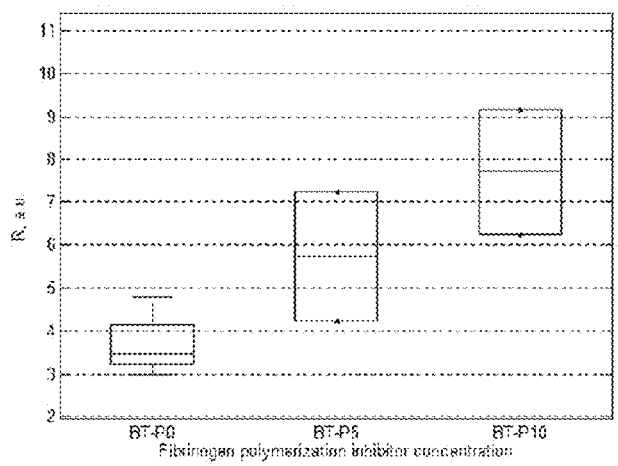

FIG. 6 a drawing substitute graph showing the relationship between the parameter R and added fibrinogen polymerization inhibitors (BT-P0, BT-P5, and BT-P10) in the case of performing measurement at the dielectric constant of 10 MHz.

Figure 7:
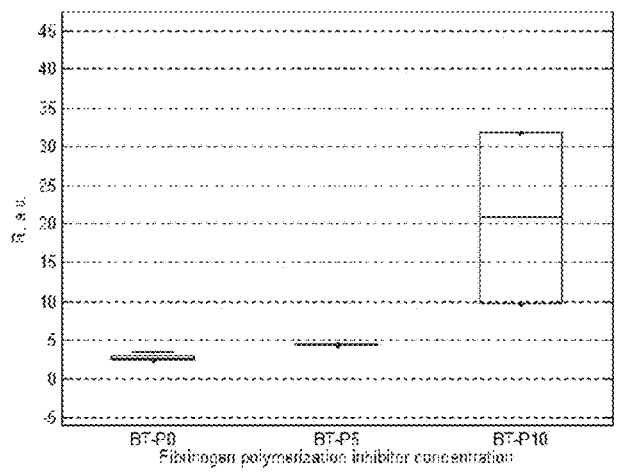

FIG. 7 a drawing substitute graph showing the relationship between the parameter R and added fibrinogen polymerization inhibitors (BT-P0, BT-P5, and BT-P10) in the case of performing measurement at the dielectric constant of 1 MHz by using the parameter R calculated by a calculation method different from the method of calculating the parameter R shown in FIG. 5.

Figure 8:
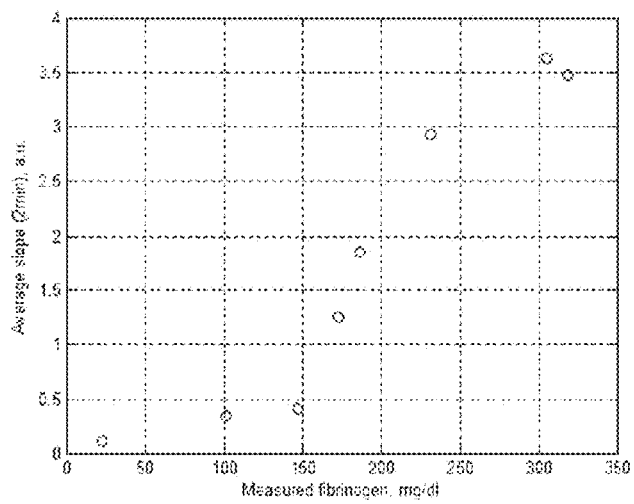

FIG. 8 is a drawing substitute graph showing the relationship between a parameter S and the fibrinogen concentration at the dielectric constant of 1 MHz.

Figure 9:
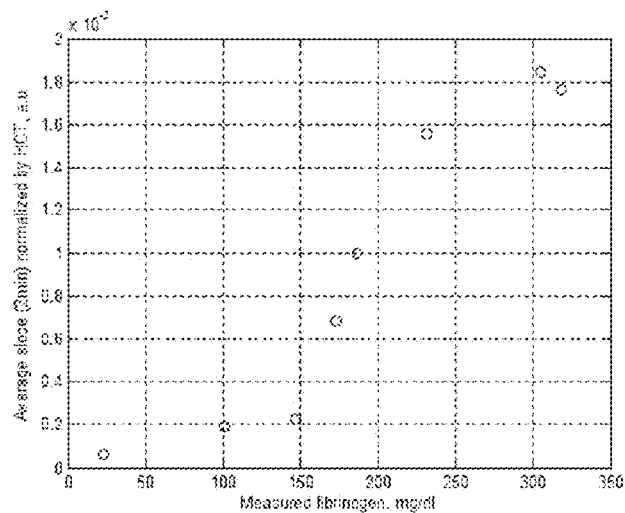

FIG. 9 is a drawing substitute graph showing the relationship between the parameter S (S_HCT) and the fibrinogen concentration at the dielectric constant of 1 MHz.

Figure 10:
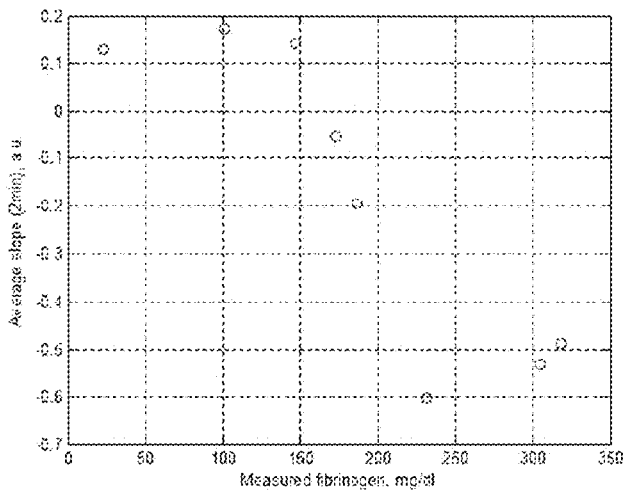

FIG. 10 is a drawing substitute graph showing the relationship between the parameter S and the fibrinogen concentration at the dielectric constant of 10 MHz.

Figure 11:
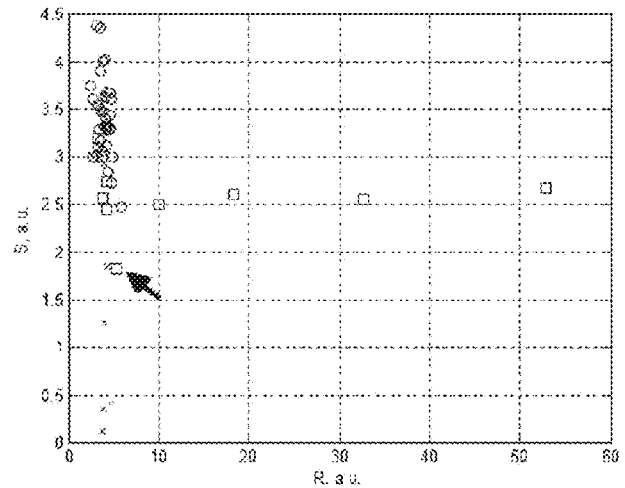

FIG. 11 is a drawing substitute graph showing the relationship between the parameter S and the parameter R.

Figure 12:
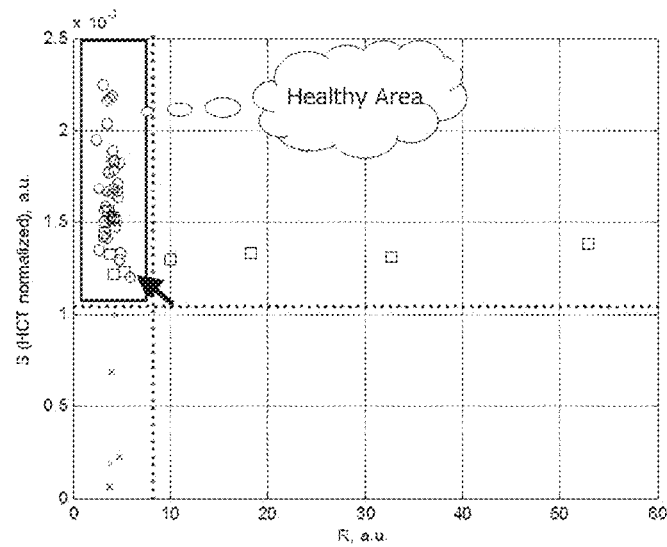

FIG. 12 is a drawing substitute graph showing the relationship between the parameter S (S_HCT) and the parameter R.

Figure 13:
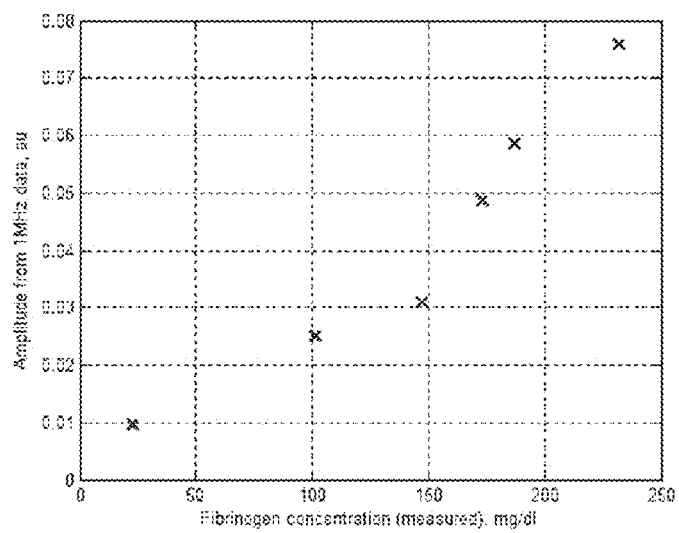

FIG. 13 is a drawing substitute graph showing the relationship between the blood clotting amplitude and the fibrinogen concentration obtained from measurement data of fibrinogen diluted samples (MB1 to MB8).

Figure 14:
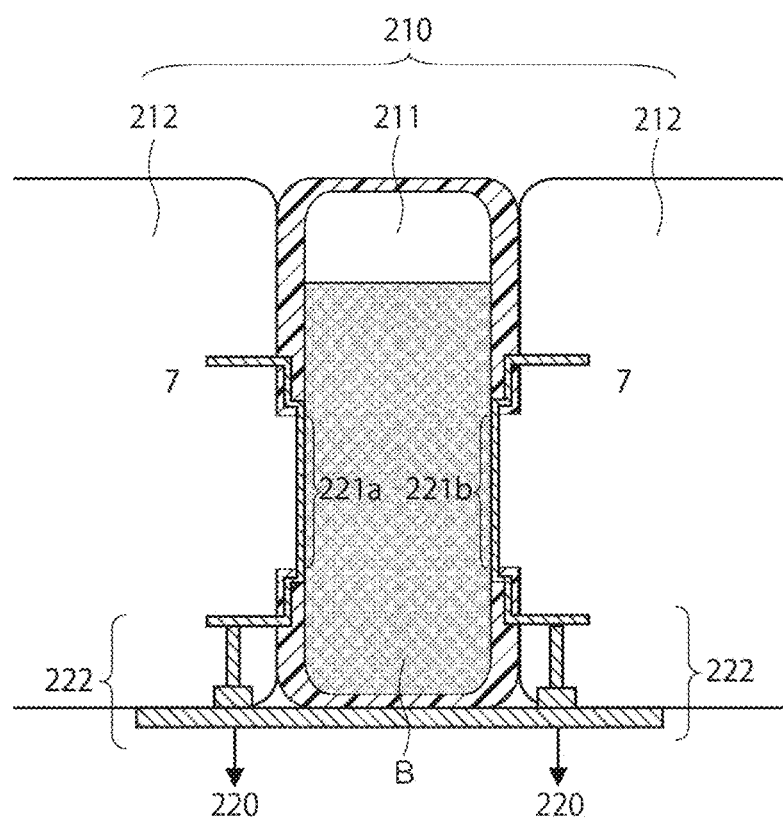

FIG. 14 is a schematic cross-sectional view schematically showing an embodiment of a blood sample holding unit 210.

Figure 15:
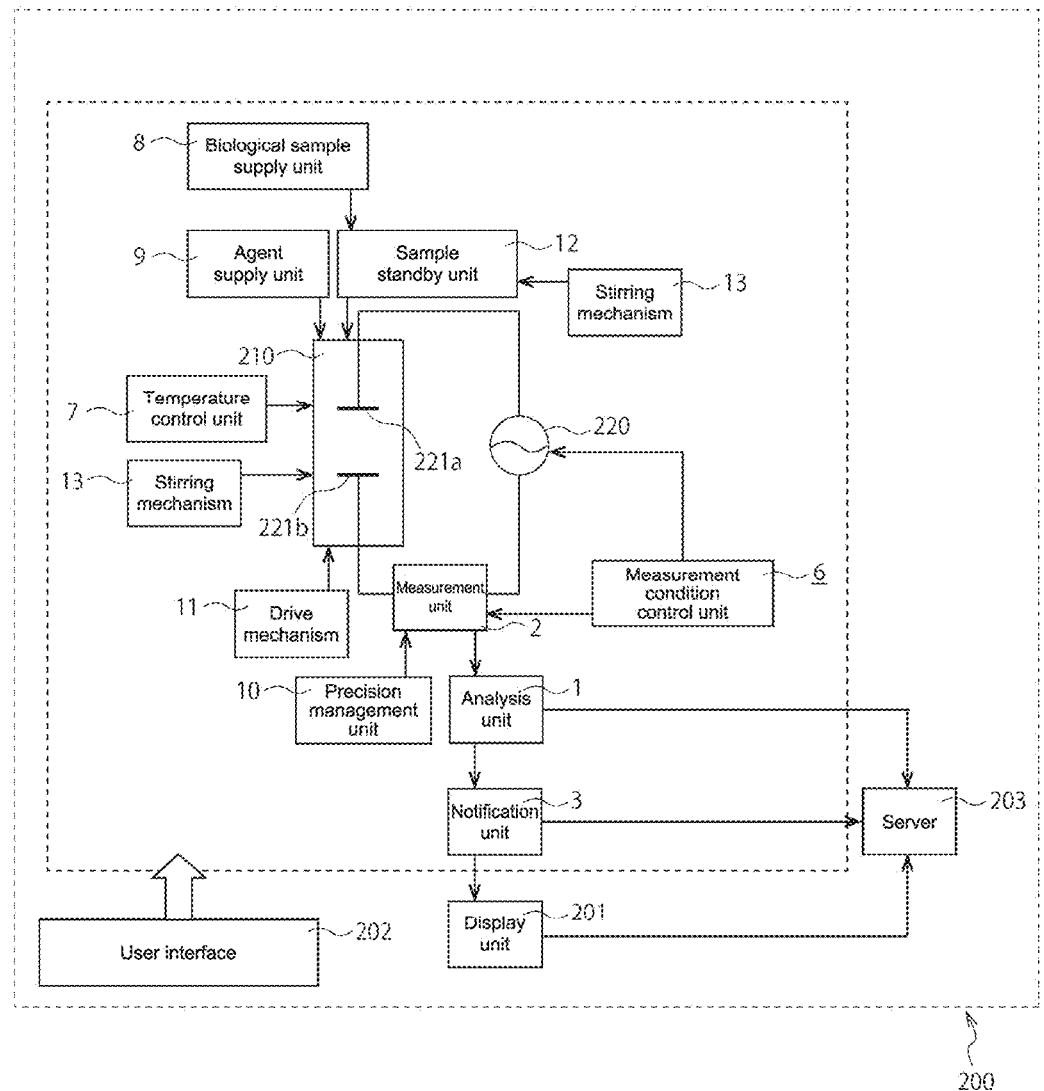

FIG. 15 is a schematic conceptual diagram schematically showing a blood state analysis system 200 according to the present technology.

Figure 16:
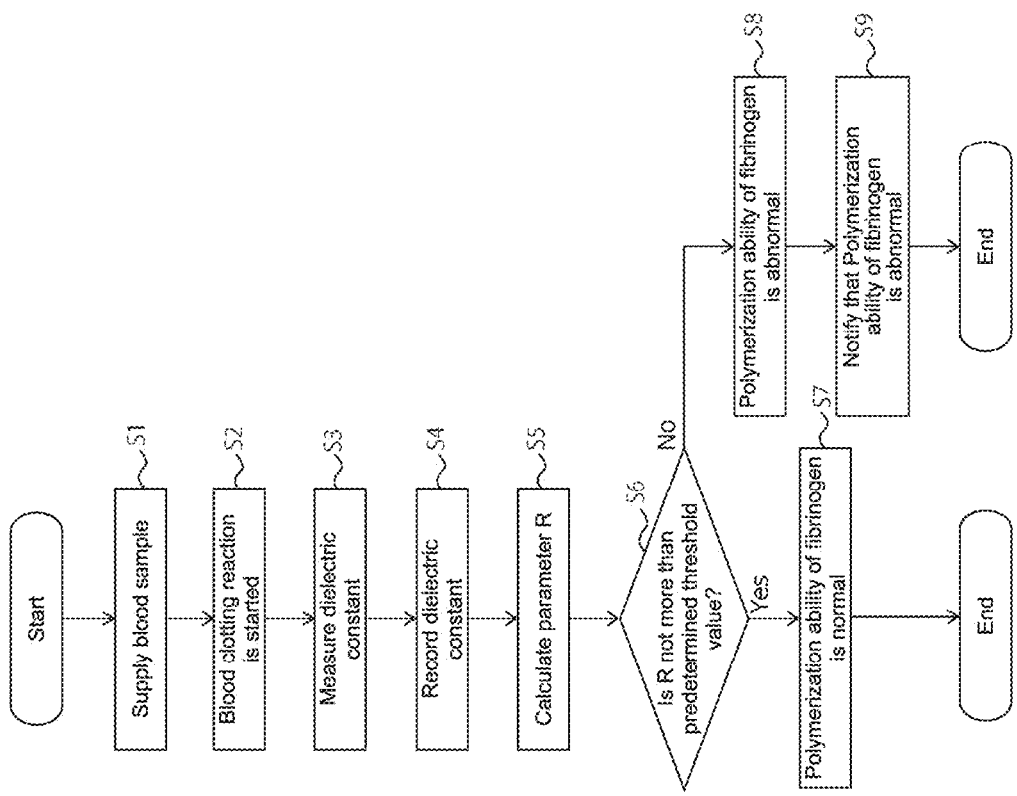

FIG. 16 is a flowchart showing an example of a blood state analysis method according to the present technology.

Figure 17:
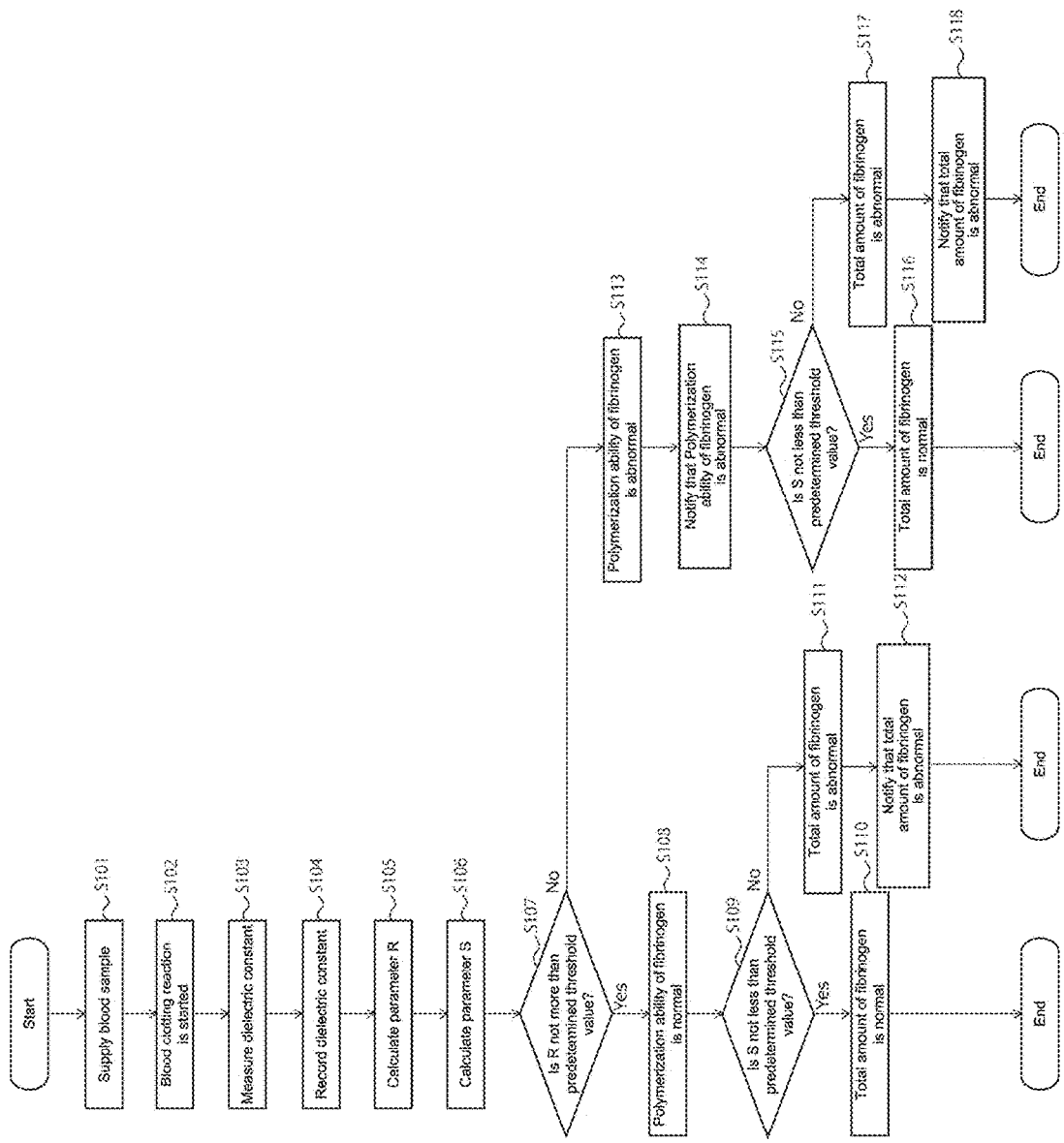

FIG. 17 is a flowchart showing a different example of the blood state analysis method according to the present technology shown in FIG. 16.

MODE(S) FOR CARRYING OUT THE INVENTION

Hereinafter, favorable embodiments for carrying out the present technology will be described with reference to the drawings. Note that the embodiments described below illustrate only examples of typical embodiments of the present disclosure, and the scope of the present technology is not narrowly interpreted by the embodiments. Note that description will be made in the following order.
1. Blood Information Analysis Apparatus 100
(1) Analysis Unit 1
[Analysis Example 1 Performed by Analysis Unit 1]
[Analysis Example 2 Performed by Analysis Unit 1]
(2) Measurement Unit 2
   (a) Blood Sample Holding Unit 210
     (a-1) Container 211
     (a-2) Container Holding Unit 212
   (b) Application Unit 220
     (b-1) Electrode 221a, 221b
(3) Notification Unit 3
(4) Display Unit 4
(5) Storage Unit 5
(6) Measurement Condition Control Unit 6
(7) Temperature Control Unit 7
(8) Blood Sample Supply Unit 8
(9) Agent Supply Unit 9
(10) Precision Management Unit 10
(11) Drive Mechanism 11
(12) Sample Standby Unit 12
(13) Stirring Mechanism 13
(14) Others 2. Blood State Analysis System 200
(1) Display Unit 201
(2) User Interface 202
(3) Server 203
3. Blood State Analysis Method
[Analysis Method Example 1]
[Analysis Method Example 2]

1. Blood State Analysis Apparatus 100

Figure 1:
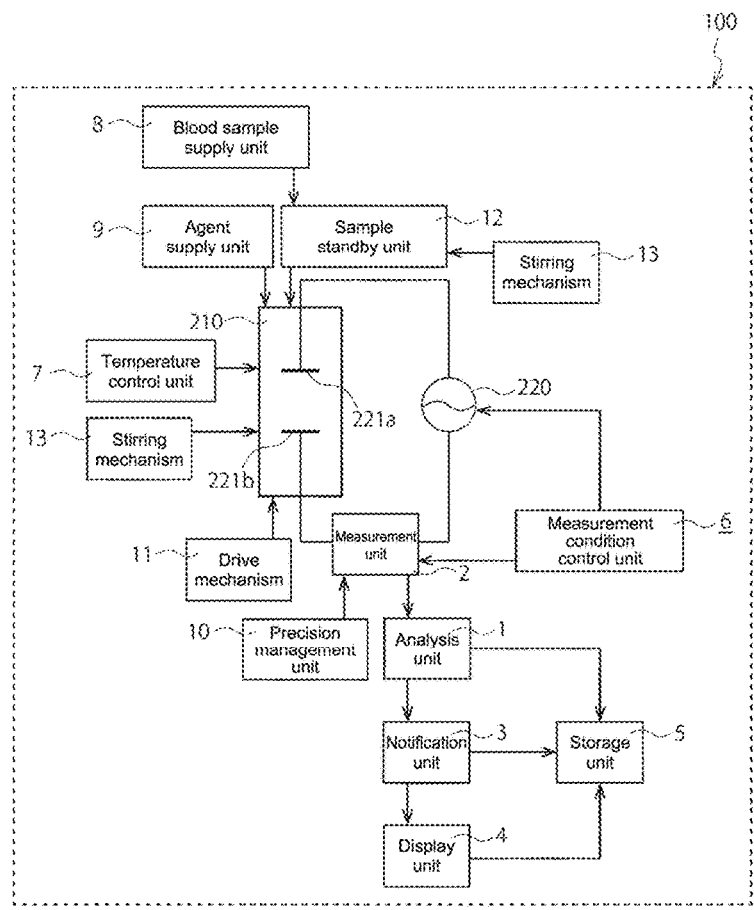
FIG. 1 is a schematic conceptual diagram schematically showing a concept of a blood information analysis apparatus 100 according to the present technology.

FIG. 1 is a schematic conceptual diagram schematically showing a concept of a blood information analysis apparatus 100 according to the present technology.

The blood state analysis apparatus 100 according to the present technology include at least an analysis unit 1. Further, as necessary, it may include a measurement unit 2, a notification unit 3, a display unit 4, a storage unit 5, a measurement condition control unit 6, a temperature control unit 7, a blood sample supply unit 8, an agent supply unit 9, a precision management unit 10, a drive mechanism 11, a sample standby unit 12, a stirring mechanism 13, and the like. Hereinafter, the respective units will be described in detail.

(1) Analysis Unit 1

The analysis unit 1 is a section that uses data related to the temporal change in electrical characteristics to analyze information related to fibrinogen in a blood sample B. The analysis unit 1 uses at least two predetermined time points derived from the data related to the temporal change on the basis of a predetermined mathematical definition to calculate a parameter R, and acquires at least two or more pieces of information related to the fibrinogen in the blood sample B. Specifically, for example, processing as shown in analysis examples 1 and 2 to be described later is performed. Accordingly, it is possible to acquire, in a single measurement, a plurality of pieces of information related to fibrinogen. As a result, in diagnosis of, for example, a pathological condition in which fibrinogen is not normally changed into fibrin while the amount itself of fibrinogen is normal, it is possible to perform examination by an easier method although the existing diagnosis requires complicated examination.

In the present technology, the blood sample B is not particularly limited, and can be freely selected as appropriate. Note that in the present technology, the "blood sample" only needs to be a sample containing red blood cells and liquid components such as plasma, and is not limited to blood itself. More specifically, examples of the "blood sample" include a liquid sample containing blood components such as whole blood, plasma, and dilutions thereof, and/or an agent additive. Examples of the agent include an anticoagulant and an agent against the anticoagulant. More specifically, examples of the agent include a calcium aqueous solution, various blood clotting factors, various coagulants, a heparin neutralizing agent, a fibrinolytic system inhibitor, a platelet inhibitor, and a platelet activating agent.

The blood state analysis apparatus 100 according to the present technology is capable of favorably measuring the electrical characteristics of, particularly, the blood sample B in a liquid state or a gel state.

In the present technology, the above-mentioned predetermined time points can be selected from, for example, (i) a time point when electrical characteristics have the maximum value or the minimum value, or a time point when a change in the electrical characteristics exceeds a predetermined threshold value (hereinafter, referred to simply as "Tstart" in some cases), (ii) a time point when the change in the electrical characteristics exceeds a predetermined change ratio set in advance, or a time point when the change in the electrical characteristics falls below the predetermined change ratio set in advance (hereinafter, referred to simply as "Tend" in some cases, (iii) a time point when the change in the electrical characteristics is the maximum, or a middle time point between the (i) and the (ii) (hereinafter, referred to simply as "Tmiddle" in some cases), and (iv) a time point when the change rate has reached the maximum rate between the (i) and the (ii) (hereinafter, referred to simply as "Tmax gradient").

The change in the electrical characteristics may be, specifically, the decrease rate of dielectric constant, the increase rate of dielectric constant, or the like. In this case, for example, it is also possible to use the first-order derivative (slope) of the measured value, and the like as an indicator. Further, the above-mentioned predetermined change ratio can be freely set to, for example, 50 to 100%, favorably 80 to 90% (of the maximum value of the decrease rate or increase rate of dielectric constant) by a user as appropriate. More specifically, as shown in the following analysis example 1, for example, it is conceivable to set Tend to the time point when the decrease rate of dielectric constant is reduced by 90% from the maximum. Note that in the present technology, the time points represented by Tstart, Tend, Tmiddle, and Tmax gradient may overlap with each other in some cases.

Further, the analysis unit 1 is capable of performing analysis by comparing at least two predetermined time points selected from Tstart, Tend, Tmiddle, and Tmax gradient with each other on the basis of a predetermined starting point. The predetermined starting point may be, for example, a time point when the value of the electrical characteristics starts decreasing or increasing, a time point when the decrease rate of dielectric constant is the maximum, or the like (hereinafter, referred to simply as "T1" in some cases). Note that in the present technology, the time point represented by T1 may overlap with the above-mentioned time point represented by Tstart, Tend, Tmiddle, or Tmax in some cases.

In the present technology, the above-mentioned information is not particularly limited as long as it is related to fibrinogen. Examples of the information include at least two pieces of information selected from information related to the total amount of fibrinogen, information related to the amount of fibrinogen involved in blood clotting, and information related to the polymerization ability of fibrinogen. The above-mentioned polymerization ability of fibrinogen is, for example, a polymerization rate of fibrinogen or the like. Acquiring these pieces of information is useful for the diagnosis of the pathological condition in which fibrinogen is not normally changed into fibrin while the amount itself of fibrinogen is normal as described above In the present technology, the value measured as the electrical characteristics can be appropriately selected depending on the purpose of analysis and the like. More specifically, for example, the value may be, for example, a value of impedance, a value of dielectric constant, or the like. In the present technology, among these, the electrical characteristics may be, particularly, a dielectric constant (e.g., 100 kHz to 10 MHz, favorably 500 kHz to 10 MHz) at a specific frequency.

Hereinafter, analysis performed by the analysis unit 1 will be described with specific examples.

Analysis Example 1 Performed by Analysis Unit 1

In this analysis example 1, an experiment for reproducing a fibrinogen polymerization disorder was performed. First, samples containing fibrinogen polymerization inhibitors were prepared. Specifically, three types of samples obtained by adding fibrinogen polymerization inhibitors (Pefabloc FG) having three different concentrations (final concentrations of BT-P0: 0 mg/mL, BT-P5: 0.5 mg/mL, and BT-P10: 1 mg/mL) to blood of a healthy subject were prepared. Next, these samples were reacted with a platelet inhibitor (Cytochalasin; final concentration of 10 µM) and an extrinsic coagulation acceleration factor (Tissue Factor).

After that, for example, the blood clotting process at a specific frequency was measured by the measurement unit 2 to be described later, and the data related to the temporal change as shown in FIGS. 2 to 4 was acquired. Part A (upper side) of FIG. 2 is a drawing substitute graph showing data related to the temporal change of the first 10 minutes of the blood clotting reaction at the dielectric constant of 1 MHz in the case of measuring blood of a healthy subject, and Part B (lower side) of FIG. 2 is a drawing substitute graph showing the first-order derivative of the data related to the temporal change shown in Part A of FIG. 2. Further, Part A (upper side) of FIG. 3 is a drawing substitute graph showing the data related to the temporal change of the blood clotting reaction at the dielectric constant of 1 MHz in the case of measuring those to which blood clotting fibrinogen polymerization inhibitors having three concentrations are added, and Part B (lower side) of FIG. 3 is a drawing substitute graph showing the first-order derivative of the data related to the temporal change shown in Part A of FIG. 3. Further, Part A (upper side) of FIG. 4 is a drawing substitute graph showing data related to the temporal change of the first 10 minutes of the blood clotting reaction at the dielectric constant of 10 MHz in the case of measuring blood of a healthy subject, and Part B (lower side) of FIG. 4 is a drawing substitute graph showing the first-order derivative of the data related to the temporal change shown in Part A of FIG. 4.

Then, the data related to the temporal change as shown in FIGS. 2 to 4 is analyzed by the analysis unit 1 to obtain a time point (T1) when the dielectric constant starts decreasing, a time point (Tmiddle) when the decrease rate or increase rate of dielectric constant is the maximum, and a time point (Tend) when the decrease rate of dielectric constant is reduced by 90% from the maximum as shown in FIGS. 2 and 4. Note that, for example, in the case where the measurement is performed at the dielectric constant of 1 MHz, Tmiddle is a time point when the decrease rate of dielectric constant is the maximum as shown in FIG. 2. Meanwhile, in the case where the measurement is performed at the dielectric constant of 10 MHz, Tmiddle is a time point when the increase rate of dielectric constant is the maximum as shown in FIG. 4.

After that, by using these parameters (Tmiddle, Tend, and T1), the parameter R was calculated on the basis of, for example, the following formula (1).

(Math. 1)

$$R = \frac{Tend - T1}{Tmiddle - T1} \quad (1)$$

Then, by using this parameter R, the relationship with the fibrinogen polymerization inhibitors was evaluated. Specifically, for example, after calculating the parameter R on the basis of data related to the temporal change as shown in FIG. 3, data as shown in FIG. 5 (drawing substitute graph showing the relationship between the parameter R and added fibrinogen polymerization inhibitors (BT-P0, BT-P5, and BT-P10) in the case of performing measurement at the dielectric constant of 1 MHz) is acquired. In FIG. 5, it can be confirmed that the parameter R increases depending on the concentration of the fibrinogen polymerization inhibitor in the case where the polymerization inhibitor is added, as compared with the sample containing no fibrinogen polymerization inhibitor.

Note that although the data shown in FIG. 5 is the parameter R obtained from the analysis result at the dielectric constant of 1 MHz, the parameter R obtained from the analysis result at the dielectric constant of 10 MHz as shown in, for example, the data in FIG. 6 can be used in the present technology.

From the above, by using the parameter R, it is possible to determine whether or not there is a fibrinogen polymerization disorder in blood clotting. Note that in the present technology, the parameter R is not limited to the above-mentioned formula (1) as long as it reflects the shape of the blood clotting curve as shown in the above-mentioned (i) to (iv), such as the time from the start of blood clotting to the point of the maximum blood clotting rate, and the time, which includes the time corresponding to the blood clotting shape, to the end of the blood clotting thereafter.

As another example of calculating the parameter R, for example, a time point (T1) when the decrease rate of dielectric constant is the maximum, a time point (Tmiddle) when the decrease rate of dielectric constant is reduced by 50% from the maximum (time point when the slope becomes half), and a time point (Tend) when the decrease rate of dielectric constant is reduced by 90% from the maximum are obtained. After that, the parameter R can be calculated on the basis of the above-mentioned formula (1) to acquire the data as shown in FIG. 7.

Analysis Example 2 Performed by Analysis Unit 2

In this analysis example 2, first, an experiment for reproducing low fibrinogen was performed by a plasma dilution method. First, samples containing fibrinogen having a plurality of concentrations were prepared. Specifically, plasma was separated from blood of a healthy subject, diluted with NaCl, and then returned to the blood to prepare samples having the characteristics shown in the following Table 1. Hematocrit % (HCT) and the platelet count (PLT) of the samples were measured by the blood cell counter, and the fibrinogen (Fbg) concentration was measured using DRI Hemato measurement or the like.

TABLE 1

|  | Aliquot | PPP (uL) | NaCl (uL) | Hct (%) | PLT (e4/uL) | Fbg concentration (mg/dL) |
| --- | --- | --- | --- | --- | --- | --- |
| MB1 | FIB_xxx | 0 | 0 | 43.6 | 17.6 | 319 |
| MB2 | FIB_020 | 0 | 900 | 40.8 | 13.6 | 101 |
| MB3 | FIB_050 | 120 | 780 | 41.6 | 15.2 | 147 |
| MB4 | FIB_080 | 240 | 660 | 42.4 | 16.4 | 173 |
| MB5 | FIB_100 | 320 | 580 | 40.4 | 15.2 | 187 |
| MB6 | FIB_150 | 520 | 380 | 41.2 | 15.6 | 232 |
| MB7 | FIB_200 | 900 | 0 | 42.8 | 16.0 | 305 |
| MB8 | FIB_000 | 0 | 900 | 38.4 | 9.2 | 23 |

Note that in Table 1, "PPP" represents an abbreviation of platelet poor plasma.

These samples (MB1 to MB8) were reacted with a platelet inhibitor (Cytochalasin; final concentration of 10 µM) and an extrinsic coagulation acceleration factor (Tissue Factor). After that, for example, the blood clotting process at a specific frequency was measured by the measurement unit 2 to be described later, and the data related to the temporal change was obtained.

Then, an increase slope s(t) of the first two minutes (time point until the dielectric constant reaches the maximum value) was obtained from the blood clotting curve measured at the dielectric constant of 1 MHz, and the parameter S (Average slope) was calculated by, for example, the following formula (2).

(Math. 2)

$$S=\text{mean}(s(t=0 \rightarrow t=120 \text{ s})) \quad (2)$$

After that, as shown in FIG. 8 (drawing substitute graph showing the relationship between the parameter S and the fibrinogen concentration at the dielectric constant of 1 MHz.), the parameter S (that may be S_HCT) was compared with the measured fibrinogen concentration (by DRI Hemato measurement). In FIG. 8, it can be confirmed that the fibrinogen concentration can be calculated from the slope (Rouleaux formation rate) before blood clotting.

Note that in the present technology, as shown in FIG. 9 (drawing substitute graph showing the relationship between the parameter S (S_HCT) and the fibrinogen concentration at the dielectric constant of 1 MHz), as the parameter S, a value normalized by HCT (S_HCT: slope normalized with a value at a time 0 corresponding to HCT) may be used. This is useful, for example, when comparing with samples with HCT that largely fluctuates.

Further, the data shown in FIG. 8 is the parameter S acquired from the analysis result at the dielectric constant of 1 MHz. However, in the present technology, as shown in, for example, the data in FIG. 10, the parameter S calculated using the time point until the dielectric constant reaches the minimum value on the basis of the analysis result at the dielectric constant of 10 MHz may be used.

From the above, it is possible to evaluate fibrinogen in the sample on the basis of the rouleaux formation rate before coagulation. Note that in the present technology, the parameter S is not limited to the above-mentioned formula (2) as long as it reflects the rouleaux formation rate. Specifically, for example, the change ratio in a predetermined time can be used.

Further, in this analysis example 2, although the increase slope s(t) is obtained on the basis of the first two minutes, the present technology is not limited thereto, and another time zone, which may be one time point, may be used as long as it is before blood clotting is started (at a time point before the dielectric constant reaches the maximum value or the minimum value). Further, in the above-mentioned formula (2), although the parameter S is calculated using the average of s(t), the present technology is not limited thereto, and a calculation method of, for example, a Median (median value) or the maximum value (Max)+the minimum value (Min)/2 may be used.

In the present technology, in calculating HCT, it is favorable to use a frequency of 2 to 5 MHz, and it is more favorable to use a frequency of 2 MHz. Further, it is also possible to use frequencies other than the frequency for the rouleaux evaluation.

In this analysis example 2, next, samples prepared from patients other than the above-mentioned samples were used, and all the samples were reacted with a platelet inhibitor (Cytochalasin; final concentration of 10 μM) and an extrinsic acceleration factor (Tissue Factor). After that, for example, the blood clotting process at a specific frequency was measured by the measurement unit 2 to be described later, and the data related to the temporal change was obtained. Then, the parameter R was calculated by a procedure similar to that in the analysis example 1, and the parameter S was calculated by the above-mentioned procedure.

The samples containing fibrinogen polymerization inhibitors shown in the analysis example 1 and the above-mentioned fibrinogen diluted samples (MB1 to MB8) were collectively evaluated by comparing the two parameters (R and S) thereof. FIG. 11 is a drawing substitute graph showing the relationship between the parameter S and the parameter R. In FIG. 11, data points of "Δ" represent the results of measuring the samples containing fibrinogen polymerization inhibitors, data points of "x" represent the results of measuring the above-mentioned fibrinogen diluted samples, and data points of "○" represent the results of measuring the patient samples. The vertical axis (parameter S) reflects the fibrinogen concentration in the sample, and the horizontal axis (parameter R) reflects the degree of fibrinogen polymerization inhibition. Further, since a data point (data point of "□") indicated by an arrow in FIG. 11 has a low HCT, the parameter S needs to be normalized by HCT as described above.

In this regard, by normalizing the parameter S by HCT in the method as described above, the data shown in FIG. 12 can be acquired. As shown in FIG. 12, a data point of "□" indicated by an arrow is in the healthy area by the normalization with HCT, and negative judgement has been changed into positive judgement. Note that in FIG. 12, the part surrounded by a rectangle represents the healthy area.

From the above, referring to FIG. 12, for example, the following determination algorithm can be created. The parameter R was compared with the Rthreshold=3. Note that in the present technology, the threshold value of the parameter can be separately determined in advance. In this analysis example 2, the threshold value is set to "3" on the basis of the distribution result of the data related to the patient samples.

In the case where R<Rthreshold, it was determined that "fibrinogen polymerization is normal", and in the case where R>Rthreshold, it was determined that "there is a possibility that there is a disorder of fibrinogen polymerization".

Further, the parameter S was compared with the Sthreshold=1.

In the case where S<Sthreshold, it was determined that "there is a possibility that the total amount of fibrinogen is less than the normal amount", and in the case where S>Sthreshold, it was determined that "the total amount of fibrinogen is normal".

By using these determinations together, for example, it is possible to perform determination because it falls under any of the determination condition of the following Table 2.

TABLE 2

| | There is possibility that there is disorder of fibrinogen polymerization | Fibrinogen polymerization is normal |
|---|---|---|
| There is possibility that total amount of fibrinogen is less than normal amount | S < Sthreshold<br>R > Rthreshold | S < Sthreshold<br>R < Rthreshold |
| Total amount of fibrinogen is normal | S > Sthreshold<br>R > Rthreshold | S > Sthreshold<br>R < Rthreshold |

Further, in this analysis example 2, a parameter A calculated on the basis of the blood clotting amplitude (Amplitude) of the data related to the temporal change can be additionally used for analysis.

Specifically, first, the above-mentioned fibrinogen diluted samples (MB1 to MB8) were reacted with a platelet inhibitor (Cytochalasin; final concentration of 10 μM) and an extrinsic coagulation acceleration factor (Tissue Factor). After that, for example, the blood clotting process at a specific frequency was measured by the measurement unit 2 to be described later, and the data related to the temporal change was obtained. Then, the parameters R and S were calculated in the above-mentioned procedure.

Further, the parameter A was calculated by the following formula (3). Note that in the following formula (3), A (T1) represents the blood clotting amplitude at T1 (e.g., time point when the dielectric constant starts decreasing), and A (Tend) represents the blood clotting amplitude at Tend (e.g., time point when the decrease rate of dielectric constant is reduced by 90% from the maximum).

(Math. 3)

$$A = \frac{A(T1) - A(Tend)}{A(T1)} \quad (3)$$

After that, for all the samples, the fibrinogen concentration was measured using DRI Hemato measurement or the like. FIG. 13 is a drawing substitute graph showing the relationship between the blood clotting amplitude and the fibrinogen concentration obtained from measurement data of the above-mentioned fibrinogen diluted samples (MB1 to MB8). It can be confirmed that in the area shown in FIG. 13, the two show a very good correlation.

From the above, it can be seen that the parameter A reflects the amount of fibrinogen involved in blood clotting. In the present technology, by further using the parameter A, for example, as described above, since the parameter S reflects the total amount of fibrinogen, by comparing the parameter A and the parameter S, it is also possible to calculate the amount of fibrinogen that is not involved in blood clotting. This is useful for, for example, diagnosis of the pathological condition of dysfibrinogemia.

In addition, in the present technology, it is also possible to use other parameters corresponding to the parameter A in combination with the parameter R and/or the parameter S.

(2) Measurement Unit 2

The blood state analysis apparatus 100 may further include the measurement unit 2. The measurement unit 2 is a section that measures the electrical characteristics of the blood sample B over time. The configuration of the measurement unit 2 can be freely designed as appropriate as long as the measurement unit 2 is configured to be capable of measuring the electrical characteristics of the blood sample B to be measured. For example, in the case of measuring impedance and a dielectric constant as the electrical characteristics, an impedance analyzer, a network analyzer, or the like can be adopted as the measurement unit 2.

More specifically, for example, the measurement unit 2 may be configured to measure the impedance of the blood sample B acquired by applying alternating voltage to the blood sample B by an application unit 220 to be described later, and measure the impedance of the blood sample B between electrodes 221a and 221b with the start time of the time point when an instruction to start measurement is received or the time point when the power of the apparatus 100 is turned on. Then, a dielectric constant and the like can be derived from the measured impedance. In order to derive the dielectric constant, a well-known function or relational formula showing the relationship between the impedance and the dielectric constant can be used.

Further, the measurement unit 2 is also capable of performing multiple measurement. Examples of the method of performing the multiple measurement include a method of simultaneously performing the multiple measurement by a plurality of provided measurement units 2, a method of performing the multiple measurement by causing one measurement unit 2 to perform scanning, a method of performing the multiple measurement by causing a blood sample holding unit 210 to be described later to move, and a method of selecting, by switching, one or more measurement units 2 that actually perform measurement from the plurality of provided measurement units 2.

(a) Blood Sample Holding Unit 210

The measurement unit 2 may include the blood sample holding unit 210. The blood sample holding unit 210 is a section that holds the blood sample B to be measured.

In the blood state analysis apparatus 100 according to the present technology, the number of blood sample holding units 210 is not particularly limited, and one or more blood sample holding units 210 can be freely arranged depending on the amount or type of the blood sample B to be measured, the measurement purpose, and the like.

In the blood state analysis apparatus 100 according to the present technology, the electrical characteristics are measured while the blood sample holding unit 210 holds the blood sample B. For that reason, the blood sample holding unit 210 is favorably configured to be sealable while holding the blood sample B. However, the blood sample holding unit 210 does not necessarily need to be hermetic as long as it is capable of staying for the time required for measuring the electrical characteristics of the blood sample B and there is no influence on the measurement.

A specific method of introducing the blood sample B into the blood sample holding unit 210 and a specific method of sealing the blood sample holding unit 210 are not particularly limited, and the blood sample B can be introduced by a free method depending on the form of the blood sample holding unit 210. Examples of such a method include a method of sealing the blood sample holding unit 210 by providing a lid portion in the blood sample holding unit 210, introducing the blood sample B by using a pipette or the like, and then closing the lid portion, and a method of sealing the blood sample holding unit 210 by introducing an injection needle from the outer surface of the blood sample holding unit 210, injecting the liquid blood sample B, and then blocking, with grease or the like, the part through which the injection needle has penetrated.

The form of the blood sample holding unit 210 is not particularly limited as long as the blood sample B to be measured can be held in the apparatus, and can be designed in a free form. For example, one or more cells provided on a substrate can be made to function as the blood sample holding unit 210, or one or more containers can be made to function as the blood sample holding unit 210. Hereinafter, one form of the blood sample holding unit 210 will be described with reference to FIG. 14.

FIG. 14 is a schematic cross-sectional view schematically showing a form of the blood sample holding unit 210. The blood sample holding unit 210 shown in FIG. 14 includes a container 211 and a container holding unit 212.

Note that in the blood state analysis apparatus 100 according to the present technology, by designing a container holding unit 210 so that a well-known cartridge type container for measurement can be used as the container 211, it is possible to cause only the container holding unit 212 to function as the blood sample holding unit 210. That is, in the present technology, the blood sample holding unit 210 includes only the container 211, includes the container 211 and the container holding unit 212, or includes only the container holding unit 212.

(a-1) Container 211

In the case of using the container 211 as the blood sample holding unit 210, the specific form thereof is not particularly limited and can be freely designed as appropriate depending on the state or type of the blood sample B, and the like as long as the blood sample B to be measured can be held. Examples of the specific form include a cylindrical body, a polygonal cylinder with a polygonal (triangular, square or more) cross section, a cone, a polygonal pyramid with a polygonal (triangular, square or more) cross section, and a combination of one or more kinds thereof.

Further, also the material forming the container 211 is not particularly limited, and can be freely selected within a range that does not affect the state or type of the blood sample B to be measured, the measurement purpose, and the like. In particular, in the present technology, it is favorable to use resin to form the container 211 from the viewpoint of easy of processing, and the like. In the present technology, also the type of resin that can be used is not particularly limited, and one or more kinds of resin applicable for holding the blood sample B can be freely selected as appropriate and used. Examples of the resin include hydrophobic and insulating polymers such as polypropylene, polymethyl methacrylate, polystyrene, acrylic, polysulfone, and polytetrafluoroethylene, copolymers, and blended polymers.

In the present technology, among these, it is particularly favorable to form the blood sample holding unit 210 with one or more kinds of resin selected from polypropylene, polystyrene, acrylic, and polysulfone. Since these kinds of resin have low coagulation activity against blood, they can be favorably used for measuring the blood sample.

(a-2) Container Holding Unit 212

In the case of using the container holding unit 212 as the blood sample holding unit 210, the specific form thereof is not particularly limited and can be freely designed as long as it is capable of holding the container 211 containing the blood sample B to be measured.

Further, also the material forming the container holding unit 212 is not particularly limited and can be freely selected depending on the form of the container 211 held by the container holding unit 212, and the like.

(b) Application Unit 220

The measurement unit 2 may include the application unit 220. The application unit 220 is a section that applies alternating voltage to a pair of electrodes 221a and 221b in contact with the blood sample B held by the blood sample holding unit 210. More specifically, for example, the application unit 220 applies voltage to the pair of electrodes 221a and 221b at the start time of the time point when an instruction to start measurement is received or the time point when the power of the apparatus 10 is turned on. More specifically, the application unit 220 applies alternating voltage of a set frequency or a frequency controlled by the measurement condition control unit 6 to be described later to the electrodes 221a and 221b for each set measurement interval or a measurement interval controlled by the measurement condition control unit 6 to be described later.

(b-1) Electrode 221a and 221b

The electrodes 221a and 221b are brought into contact with the blood sample B at the time of measurement, and used for applying necessary voltage to the blood sample B. In the present technology, the number of electrodes 221a and 221b is not particularly limited as long as they are capable of measuring the impedance of the blood sample B, and more than one pair of electrodes can be freely arranged.

Further, also the arrangement, form, and the like of the electrodes 221a and 221b are not particularly limited, and the electrodes 221a and 221b can be freely designed as appropriate depending on the form of the blood sample holding unit 210, and the like as long as they are capable of applying necessary voltage to the blood sample B. For example, as in the blood sample holding unit 210 shown in FIG. 14, the electrodes 221a and 221b may be integrated with the blood sample holding unit 210 (container 211). Alternatively, although not shown, by providing the electrodes 221a and 221b on the lid portion of the container 211 and sealing the electrodes 221a and 221b with the lid portion, the electrodes 221a and 221b may be brought into contact with the blood sample B contained in the container 211. Alternatively, by inserting the pair of electrodes 221a and 221b from the outside of the container 211 into the container 211 at the time of measurement, the electrodes 221a and 221b may be brought into contact with the blood sample B.

Also the material forming the electrodes 221a and 221b is not particularly limited, and one or more well-known electrically conductive materials can be freely selected as appropriate within a range that does not affect the state or type of the blood sample B to be measured, the measurement purpose, and the like, and used. Examples of the material include titanium, aluminum, stainless steel, platinum, gold, copper, and graphite.

In the present technology, among these, it is particularly favorable to form the electrodes 221a and 221b with an electrically conductive material containing titanium. Since titanium has low coagulation activity against blood, it can be favorably used for measuring the blood sample B.

(b-2) Connection Unit 222

A connection unit 222 is a section that electrically connects the application unit 220 and the electrodes 221a and 221b. The specific form of the connection unit 222 is not particularly limited, and can be designed in a free form as appropriate as long as it is capable of electrically connecting the application unit 220 and the electrodes 221a and 221b.

(3) Notification Unit 3

The blood state analysis apparatus 100 may further include the notification unit 3. The notification unit 3 is a section that notifies the analysis result by the analysis unit 1 at a specific time point. In the present technology, the configuration of the notification unit 3 is not particularly limited. For example, the notification unit 3 may be configured to generate a notification signal only in the case where an abnormal analysis result is obtained during measurement, and notify a user of the result in real time. With this configuration, since the user is notified of the analysis result only at the specific time point when the abnormal analysis result has been determined, the usability is improved.

Further, also the method of notifying the user is not particularly limited. For example, the user may receive the notification via the display unit 4 to be described later, a display, a printer, a speaker, lighting, or the like. Further, for example, a device having a communication function of transmitting an e-mail or the like for notifying that a notification signal has been generated to a mobile device such as a cellular phone and a smartphone may be used together with the notification unit 3.

(4) Display Unit 4

The blood state analysis apparatus 100 may further include the display unit 4. The display unit 4 is a section that displays the analysis result by the analysis unit 1, the data related to the temporal change in electrical characteristics measured by the measurement unit 2, the notification result from the notification unit 3, and the like. The configuration of the display unit 4 is not particularly limited. For example, as the display unit 4, a display, a printer, or the like can be adopted. Further, in the present technology, the display unit 4 is not necessarily need to be provided, and an external display apparatus may be connected.

(5) Storage Unit 5

The blood state analysis apparatus 100 may further include the storage unit 5. The storage unit 5 is a section that stores the analysis result by the analysis unit 1, the data related to the temporal change in electrical characteristics measured by the measurement unit 2, the notification result from the notification unit 3, and the like. The configuration of the storage unit 5 is not particularly limited. For example, as the storage unit 5, a hard disk drive, a flash memory, an SSD (Solid State Drive), or the like can be adopted. Further, in the present technology, the storage unit 5 is not necessarily need to be provided, and an external storage apparatus may be connected.

Further, in the present technology, an operation program and the like of the blood state analysis apparatus 100 may be stored in the storage unit 5. For example, the storage unit 5 may have a function of outputting the parameters R, S and/or A calculated by the analysis unit.

(6) Measurement Condition Control Unit 6

The blood state analysis apparatus 100 may further include the measurement condition control unit 6. The measurement condition control unit 6 is a section that controls the measurement time and/or the measurement frequency, and the like in the measurement unit 2.

As a specific method of controlling the measurement time, the measurement interval can be controlled depending on the amount of data necessary for the target analysis, and the like, or the timing of finishing the measurement can be controlled in the case where, for example, the measurement value has been substantially leveled off.

Further, it is also possible to control the measurement frequency depending on the type of the blood sample B to be measured, the measurement value necessary for the target analysis, and the like. Examples of the method of controlling the measurement frequency include a method of changing the frequency of alternating voltage to be applied between the electrodes 221a and 221b, and a method of superimposing a plurality of frequencies to measure the impedance at the plurality of frequencies. Examples of the specific method include a method of arranging a plurality of single-frequency analyzers side by side, a method of sweeping a frequency, a method of superimposing frequencies and extracting information of each frequency with a filter, and a method of performing measurement by using the response to impulse.

(7) Temperature Control Unit 7

The blood state analysis apparatus 100 may further include the temperature control unit 7. The temperature control unit 7 is a section that controls the temperature in the blood sample holding unit 210. In the blood state analysis apparatus 100 according to the present technology, this temperature control unit 7 is not an essential section. However, in order to keep the blood sample B to be measured in an optimal state for measurement, it is favorable to provide the temperature control unit 7.

Further, in the case of providing the sample standby unit 14 as will be described later, the temperature control unit 7 may control the temperature in the sample standby unit 14. Further, in the case where an agent is put in the blood sample B at the time of or before the measurement, the temperature control unit 7 may be provided to control the temperature of the agent. In this case, temperature control units 7 may be provided for the temperature control in the blood sample holding unit 210, the temperature control in the sample standby unit 12, and the temperature control of the agent. Alternatively one temperature control unit 7 may perform all the temperature control.

The specific method of controlling the temperature is not particularly limited. However, for example, by providing the container holding unit 212 with a temperature adjustment function, the container holding unit 212 can be made function as the temperature control unit 7.

(8) Blood Sample Supply Unit 8

The blood state analysis apparatus 100 may further include the blood sample supply unit 8. The blood sample supply unit 8 is a section that automatically supplies the blood sample holding unit 210 with the blood sample B. In the blood state analysis apparatus 100 according to the present technology, this blood sample supply unit 8 is not an essential section. However, by providing the blood sample supply unit 8, it is possible to automatically perform each step.

The specific method of supplying the blood sample B is not particularly limited. However, for example, in the case where the blood sample B is in a liquid state, it is possible to automatically supply the blood sample holding unit 210 with the blood sample B by using a pipetter and a tip attached to the end of the pipetter. In this case, in order to prevent measurement errors or the like from occurring, it is favorable that the tip is disposable. Further, it is also possible to automatically supply the blood sample B from the reservoir of the blood sample B to the blood sample holding unit 210 by using a pump or the like. Further, it is also possible to automatically supply the blood sample holding unit 210 with the blood sample B by using a permanent nozzle. In this case, in order to prevent measurement errors or the like from occurring, it is favorable to provide the nozzle with a cleaning function.

(9) Agent Supply Unit 9

The blood state analysis apparatus 100 may further include the agent supply unit 9. The agent supply unit 9 is a section that automatically supplies the blood sample holding unit 210 with one or more kinds of agents. In the blood state analysis apparatus 100 according to the present technology, this agent supply unit 9 is not an essential section. However, by providing the agent supply unit 9, it is possible to automatically perform each step.

The specific method of supplying the agent is not particularly limited, and a method similar to that of the blood sample supply unit 8 described above can be used. In particular, it is favorable to supply the agent by using a method capable of supplying a predetermined amount of agent without being in contact with the blood sample holding unit 210 (container 211). For example, in the case of a liquid agent, the agent can be discharged and supplied. More specifically, for example, it is possible to discharge and supply the liquid agent to the blood sample holding unit 210 (container 211) by introducing the liquid agent into a discharge pipe in advance and blowing, for a short time, pressurized air separately connected via a pipe line connected to the discharge pipe into the pipe line. At this time, by adjusting the air pressure and the valve opening/closing time, it is also possible to adjust the amount of liquid agent to be discharged.

Further, in addition to the blowing of air, it is also possible to discharge and supply the liquid agent to the blood sample holding unit 210 (container 211) by using vaporization of the liquid agent itself or air dissolved in it by heating. At this time, it is also possible to adjust the volume of generated bubbles and adjust the amount of liquid agent to be discharged by adjusting the voltage applied to a vaporizing chamber in which a heating element or the like is placed and the application time.

Further, it is possible to supply the blood sample holding unit 210 (container 211) with the liquid agent by driving a movable unit provided in the pipe line without using air using a piezoelectric element (piezo element) or the like, and delivering the liquid agent in an amount determined by the volume of the movable unit. Further, for example, it is also possible to supply the agent by using a so-called inkjet method in which a liquid agent is made into fine droplets and sprayed directly onto the desired blood sample holding unit 210 (container 211).

The agent supply unit 9 may be provided with a stirring function, a temperature control function, an identification function (e.g., barcode reader) for identifying, for example, the type of the agent, and the like.

Note that in the case of using an agent, a predetermined agent in a solid state or in a liquid state as it is may be contained in the container 211 in advance. For example, an anticoagulant, a coagulation initiator, or the like can be contained in the container 211 in advance. By containing an agent in the container 211 in advance, it is unnecessary to provide the agent supply unit 9 or a section that holds the agent, and it is possible to miniaturize the apparatus and reduce the cost. Further, since this reduces, for example, the trouble of the user to replace the agent and maintenance of the agent supply unit 9 or the agent holding unit is unnecessary, it is possible to improve the usability.

(10) Precision Management Unit 10

The blood state analysis apparatus 100 may further include the precision management unit 10. The precision management unit 10 is a section that manages precision of the measurement unit 2. In the electrical characteristics measurement apparatus 100 according to the present technology, this precision management unit 10 is not an essential section. However, by providing the precision management unit 10, it is possible to improve the precision of the measurement by the measurement unit 2.

The specific method of managing the precision of the measurement unit 2 is not particularly limited, and a well-known precision management method can be freely selected as appropriate and used. Examples of such a method include a method of managing the precision of the measurement unit 2 by performing calibration of the measurement unit 2, such as a method of performing calibration of the measurement unit 2 by placing a metal plate or the like for short-circuiting in the apparatus 100 and short-circuiting the electrode and the metal plate before starting measurement, a method of bringing a calibration jig or the like into contact with the electrode, and a method of performing calibration of the measurement unit 2 by placing a metal plate or the like in a container having the same form as that of the container 211 in which the blood sample B is to be put and short-circuiting the electrode and the metal plate before starting measurement.

Further, the present technology is not limited to the above-mentioned methods, and a free method, e.g., a method of managing the precision of the measurement unit 2 by checking the state of the measurement unit 2 before the actual measurement and calibrating the measurement unit 2 by performing the above-mentioned calibration or the like only when there is an abnormality, may be selected as appropriate and used.

(11) Drive Mechanism 11

The blood state analysis apparatus 100 may further include the drive mechanism 11. The drive mechanism 11 is a section to be used for moving the blood sample holding unit 210 in the measurement unit 2 depending on various purposes. For example, by moving the blood sample holding unit 210 to the direction of changing the direction of gravity applied to the blood sample B held in the blood sample holding unit 210, it is possible to prevent the measurement value from being affected by sedimentation of the sedimentation component in the blood sample B.

Further, for example, it is possible to drive the blood sample holding unit 210 so that the application unit 220 and the electrodes 221a and 221b can be disconnected from each other at the time of non-measurement and the application unit 220 and the electrodes 221a and 221b can be electrically connected to each other at the time of measurement as in the blood sample holding unit 210.

Further, for example, in the case of providing a plurality of blood sample holding units 210, by configuring the blood sample holding units 210 to be capable of moving, it is possible to perform measurement, blood sample supply, agent supply, and the like by moving the blood sample holding units 210 to necessary sections. That is, since it is unnecessary to move the measurement unit 2, the blood sample supply unit 8, the agent supply unit 9, and the like to the target blood sample holding unit 210, it is unnecessary to provide a drive unit or the like for moving the respective units and it is possible to miniaturize the apparatus and reduce the cost.

(12) Sample Standby Unit 12

The blood state analysis apparatus 100 may further include the sample standby unit 12. The sample standby unit 12 is a section in which the isolated blood sample B is caused to stand by before measurement. In the blood state analysis apparatus 100 according to the present technology, this sample standby unit 12 is not an essential section. However, by providing the sample standby unit 12, it is possible to smoothly measure the electrical characteristics.

The sample standby unit 12 may be provided with a stirring function, a temperature control function, a mechanism for moving to the blood sample holding unit 210, an identification function (e.g., barcode reader) for identifying, for example, the type of the blood sample B, an automatic opening function, and the like.

(13) Stirring Mechanism 13

The blood state analysis apparatus 100 may further include the stirring mechanism 13. The stirring mechanism 13 is a mechanism for stirring the blood sample B, and stirring the blood sample B and an agent. In the blood state analysis apparatus 100 according to the present technology, this stirring mechanism 13 is not an essential section. However, for example, in the case where the blood sample B contains a sedimentation component or the case where an agent is added to the blood sample B at the time of measurement, it is favorable to provide the stirring mechanism 13.

The specific stirring method by the stirring mechanism 13 is not particularly limited, and a well-known stirring method can be freely selected and used. Examples of such a method include stirring by pipetting, stirring using a stirring rod, a stirring bar, or the like, and stirring by reversing the container containing the blood sample B or the agent.

(14) Others

Note that functions performed by the respective units of the blood state analysis apparatus 100 according to the present technology may be stored as a program in a personal computer or a hardware resource including a control unit including a CPU and the like and a recording medium (non-volatile memory (USB memory or the like), HDD, CD, and the like), and implemented by the personal computer or the control unit.

2. Electrical Characteristics Measurement System 200

FIG. 15 is a schematic conceptual diagram schematically showing a concept of the blood state analysis system 200 according to the present technology. The blood state analysis system 200 according to the present technology roughly includes at least the measurement unit 2 and the analysis unit 1. Further, the blood state analysis system 200 may include, as necessary, the display unit 201, the user interface 202, the server 203, the notification unit 3, the measurement condition control unit 6, the temperature control unit 7, the blood sample supply unit 8, the agent supply unit 9, the precision management unit 10, the drive mechanism 11, the sample standby unit 12, the stirring mechanism 13, and the like. Hereinafter, the respective units will be described in detail. Note that since the measurement unit 2, the analysis unit 1, the notification unit 3, the measurement condition control unit 6, the temperature control unit 7, the blood sample supply unit 8, the agent supply unit 9, the precision management unit 10, the drive mechanism 11, the sample standby unit 12, and the stirring mechanism 13 are the same as those of the blood state analysis apparatus 100 described above, description thereof is omitted here.

(1) Display Unit 201

The display unit 201 is a section that displays the analysis result by the analysis unit 1, the data related to the temporal change in electrical characteristics measured by the measurement unit 2, the notification result by the notification unit 3, and the like. The configuration of the display unit 201 is not particularly limited. Note that FIGS. 2 to 13 described above show an example of the data displayed on the display unit 201.

Further, in the display unit 201, it is also possible to display the result of analyzing the physical properties or the state of the blood sample B, and the like by using the data related to the temporal change in electrical characteristics measured by the measurement unit 2.

(2) User Interface 202

The user interface 202 is a section for a user to operate. The user is capable of accessing the respective sections of the blood state analysis system 200 according to the present technology via the user interface 202.

(3) Server 203

The server 203 is a section that includes at least a storage unit that stores the data related to the temporal change acquired from the measurement unit 2 and/or the analysis result acquired from the analysis unit 1, and is connected to at least the measurement unit 2 and/or the analysis unit 1 via a network. It is also possible to improve the usability by providing the blood state analysis system 200 according to the present technology with this server 203.

Further, the server 203 is capable of managing various kinds of data uploaded from the respective sections of the blood state analysis system 200 according to the present technology and outputting the various kinds of data to the display unit 201 or the like according to an instruction from a user.

3. Blood State Analysis Method

An electrical characteristics measurement method according to the present technology is a method including at least a measuring step and an analyzing step. Since the specific method performed in the measuring step and the specific method performed in the analyzing step are respectively the same as the above-mentioned measurement method performed by the measurement unit 2 of the blood state analysis apparatus 100 and the analysis method performed by the analysis unit 1 of the apparatus 100, description thereof is omitted here. Hereinafter, an example of the analysis method using the electrical characteristics measurement method according to the present technology will be described with reference to FIG. 16 and FIG. 17.

Analysis Method Example 1

FIG. 16 is a flowchart showing an example of the electrical characteristics measurement method according to the present technology, and corresponds to the above-mentioned analysis example 1.

First, the blood sample supply unit 8 supplies the blood sample B (Step S1). Next, the agent supply unit 9 supplies an agent to start a blood clotting reaction, and blood clotting is started (Step S2). After that, the measurement unit 1 measures a dielectric constant over time (Step S3), and the storage unit 5 records the dielectric constant (Step S4). Then, the analysis unit 1 calculates the parameter R by the method shown in the above-mentioned analysis example 1 or the like (Step S5), and determines whether or not the parameter R is not more than a predetermined threshold value (Step S6).

After that, in the case where the parameter R is not more than the predetermined threshold value (R<Rthreshold) (Step S6), the analysis unit 1 determines that the polymerization ability of fibrinogen (e.g., polymerization rate of fibrinogen or the like) is normal (Step S7), and the processing is finished. Meanwhile, in the case where the parameter R is more than the predetermined threshold value (R>Rthreshold) (Step S6), the analysis unit 1 determines that the polymerization ability of fibrinogen is abnormal (Step S8), the notification unit 3 notifies the user of that the polymerization ability of fibrinogen is abnormal (Step S9), and the processing is finished.

Analysis Method Example 2

FIG. 17 is a flowchart showing a different example of the blood state analysis method according to the present technology shown in FIG. 16, and corresponds to the above-mentioned analysis example 2.

First, the blood sample supply unit 8 supplies the blood sample B (Step S101). Next, the agent supply unit 9 supplies an agent to start a blood clotting reaction, and blood clotting is started (Step S102). After that, the measurement unit 1 measures a dielectric constant over time (Step S103), and the storage unit 5 records the dielectric constant (Step S104). Then, the analysis unit 1 calculates the parameters R and S by the method shown in the above-mentioned analysis example 2 or the like (Steps S105 and S106), and determines whether or not the parameter R is not more than a predetermined threshold value first (Step S107).

After that, in the case where the parameter R is not more than the predetermined threshold value (R<Rthreshold)

(Step S107), the analysis unit 1 determines that the polymerization ability of fibrinogen (e.g., polymerization rate of fibrinogen or the like) is normal (Step S108), and then determines whether or not the parameter S is not more than a predetermined threshold value (Step S109). Then, in the case where the parameter S is not less than (S>Sthreshold) (Step S109), the analysis unit 1 determines that the total amount of fibrinogen is normal (Step S110), and the processing is finished. Meanwhile, in the case where the parameter S is less than the predetermined threshold value (S<Sthreshold) (Step S109), the analysis unit 1 determines that the total amount of fibrinogen is abnormal (Step S111), the notification unit 3 notifies the user of that the total amount of fibrinogen is abnormal (Step S112), and the processing is finished.

Further, in the case where the parameter R is more than the predetermined threshold value (R>Rthreshold) (Step S107), the analysis unit 1 determines that the polymerization ability of fibrinogen is abnormal (Step S113), the notification unit 3 notifies a user of that the polymerization ability of fibrinogen is abnormal (Step S114), and then, the analysis unit 1 determines whether or not the parameter S is not less than the predetermined threshold value (Step S115). Then, in the case where the parameter S is not less than the predetermined threshold value (S>Sthreshold) (Step S115), the analysis unit 1 determines that the total amount of fibrinogen is normal (Step S116), and the processing is finished. Meanwhile, in the case where the parameter S is less than the predetermined threshold value (S<Sthreshold) (Step S115), the analysis unit 1 determines that the total amount of fibrinogen is abnormal (Step S117), the notification unit 3 notifies the user of that the total amount of fibrinogen is abnormal (Step S118), and the processing is finished.

Note that although the step of calculating the parameter A is not described in the analysis method example 2 shown in FIG. 17, in the present technology, also the parameter A may be calculated as shown in the above-mentioned analysis example 2, and used for the analysis method according to the present technology. Further, in addition thereto, other parameters corresponding to the parameter A may be used in combination with the parameter R and/or the parameter S.

It should be noted that the present technology may take the following configurations.

(1)

A blood state analysis apparatus, including: at least an analysis unit that uses data related to a temporal change in electrical characteristics to analyze information related to fibrinogen in a blood sample, in which the analysis unit uses at least two predetermined time points derived from the data related to the temporal change on a basis of a predetermined mathematical definition to calculate a parameter R, and acquires at least two pieces of information related to the fibrinogen in the blood sample.

(2)

The blood state analysis apparatus according to (1), in which the at least two predetermined time points are selected from (i) a time point when the electrical characteristics have a maximum value or a minimum value, or a time point when a change in the electrical characteristics exceeds a predetermined threshold value, (ii) a time point when the change in the electrical characteristics exceeds a predetermined change rate set in advance, or a time point when the change in the electrical characteristics falls below the predetermined change rate set in advance, (iii) a time point when the change in the electrical characteristics is the maximum or a middle time point between the (i) and the (ii), and (iv) a time point when a maximum change rate is obtained between the (i) and the (ii).

(3)

The blood state analysis apparatus according to (2), in which the analysis unit compares the at least two predetermined time points selected from the (i) to (iv) with each other on a basis of a predetermined starting point.

(4)

The blood state analysis apparatus according to any one of (1) to (3), in which the information includes at least two pieces of information selected from information related to a total amount of fibrinogen, information related to an amount of fibrinogen involved in blood clotting, and information related to a polymerization ability of fibrinogen.

(5)

The blood state analysis apparatus according to any one of (1) to (4), in which the electrical characteristics include a dielectric constant at a specific frequency.

(6)

The blood state analysis apparatus according to any one of (1) to (5), in which the analysis unit further uses a derivative to calculate a parameter S, the derivative being obtained at a time point before the electrical characteristics has a maximum value or a minimum value.

(7)

The blood state analysis apparatus according to any one of (1) to (6), in which the analysis unit further uses a blood clotting amplitude to calculate a parameter A, the blood clotting amplitude being obtained at a predetermined time point.

(8)

A blood state analysis system, including: at least a measurement unit that measures electrical characteristics of a blood sample over time; and an analysis unit that uses data related to a temporal change in the electrical characteristics measured by the electrical characteristics measurement apparatus to analyze information related to fibrinogen in the blood sample, in which the analysis unit uses at least two predetermined time points derived from the data related to the temporal change on a basis of a predetermined mathematical definition to calculate a parameter R, and acquires at least two pieces of information related to the fibrinogen in the blood sample.

(9)

The blood state analysis system according to (8) further including a server that stores the data related to the temporal change by the electrical characteristics measurement apparatus and/or an analysis result by the blood state analysis apparatus, in which the server is connected to the electrical characteristics measurement apparatus and/or the blood state analysis apparatus via a network.

(10)

A blood state analysis method, including: at least a measurement step of measuring electrical characteristics of a blood sample over time; and an analysis step of using data related to a temporal change in the electrical characteristics acquired in the measurement step to analyze information related to fibrinogen in the blood sample, in which the analysis step further includes using at least two predetermined time points derived from the data related to the temporal change on a basis of a predetermined mathematical definition to calculate a parameter R, and acquiring at least two pieces of information related to the fibrinogen in the blood sample.

(11)

The blood state analysis method according to (10), in which the parameter is selected from (i) a time point when the electrical characteristics have a maximum value or a minimum value, or a time point when a change in the electrical characteristics exceeds a predetermined threshold value, (ii) a time point when the change in the electrical characteristics exceeds a predetermined change rate set in advance, or a time point when the change in the electrical characteristics falls below the predetermined change rate set in advance, (iii) a time point when the change in the electrical characteristics is the maximum or a middle time point between the (i) and the (ii), and (iv) a time point when a maximum change rate is obtained between the (i) and the (ii).

(12)

The blood state analysis method according to (11), in which the analysis step further includes comparing the at least two predetermined time points selected from the (i) to (iv) with each other on a basis of a predetermined starting point.

(13)

The blood state analysis method according to any one of (10) to (12), in which the information includes at least two pieces of information selected from information related to a total amount of fibrinogen, information related to an amount of fibrinogen involved in blood clotting, and information related to a polymerization ability of fibrinogen.

(14)

The blood state analysis method according to any one of (10) to (13), in which the analysis step further includes using a derivative to calculate a parameter S, the derivative being obtained at a time point before the electrical characteristics has a maximum value or a minimum value.

(15)

The blood state analysis method according to any one of (10) to (14), in which the analysis step further includes using a blood clotting amplitude to calculate a parameter A, the blood clotting amplitude being obtained at a predetermined time point.

(16)

A program that causes a computer to function as:

a measurement unit that measures electrical characteristics of a blood sample over time; and an analysis unit that uses data related to a temporal change in the electrical characteristics acquired by the measurement unit to analyze information related to fibrinogen in the blood sample, in which the analysis unit uses at least two predetermined time points derived from the data related to the temporal change on a basis of a predetermined mathematical definition to calculate a parameter R, and acquires at least two pieces of information related to the fibrinogen in the blood sample.

INDUSTRIAL APPLICABILITY

By using the present technology, it is possible to acquire, in a single measurement a plurality of pieces of information related to fibrinogen, when measuring the electrical characteristics of a blood sample.

REFERENCE SIGNS LIST

100: blood state analysis apparatus
1: analysis unit
2: measurement unit
210: blood sample holding unit
211: container
212: container holding unit
220: application unit
221a, 221b: electrode
222: connection unit
3: notification unit
4: display unit
5: storage unit
6: measurement condition control unit
7: temperature control unit
8: blood sample supply unit
9: agent supply unit
10: precision management unit
11: drive mechanism
12: sample standby unit
13: stirring mechanism
200: blood state analysis system
201: display unit
202: user interface
203: server
B: blood sample

The invention claimed is:

1. A blood state analysis method comprising:

acquiring, based on a parameter R, at least two pieces of information related to fibrinogen in a blood sample, calculating the parameter R based on a predetermined mathematical definition, using at least two predetermined time points derived from data related to a temporal change in electrical characteristics of the blood sample;

analyzing the at least two pieces of information using the data related to the temporal change in the electrical characteristics of the blood sample, wherein the electrical characteristics comprise at least one dielectric constant at frequencies of 500 kilohertz to 10 megahertz and selecting the at least two pieces of information from information related to a total amount of fibrinogen, information related to an amount of fibrinogen involved in blood clotting, and information related to a polymerization ability of fibrinogen.

2. The blood state analysis method according to claim 1, further comprising: selecting the at least two predetermined time points from a list including:

(i) a time point when the electrical characteristics have a maximum value or a minimum value, or a time point when a change in the electrical characteristics exceeds a predetermined threshold value,
(ii) a time point when the change in the electrical characteristics exceeds a predetermined change rate set in advance, or a time point when the change in the electrical characteristics falls below the predetermined change rate set in advance,
(iii) a time point when the change in the electrical characteristics is the maximum or a middle time point between the (i) and the (ii), and
(iv) a time point when a maximum change rate is obtained between the (i) and the (ii).

3. The blood state analysis method according to claim 2, wherein the method comprises:
comparing the at least two predetermined time points selected from the (i) to (iv) with each other on a basis of a predetermined starting point.

4. The blood state analysis method according to claim 1, wherein the method comprises:
using a derivative to calculate a parameter S, the derivative being obtained at a time point before the electrical characteristics have a maximum value or a minimum value.

5. The blood state analysis method according to claim 1, wherein the method comprises:
using the data includes using a blood clotting amplitude to calculate a parameter A, the blood clotting amplitude being obtained at a predetermined time point.

* * * * *